US008597219B2

(12) United States Patent
Hargrave et al.

(10) Patent No.: US 8,597,219 B2
(45) Date of Patent: Dec. 3, 2013

(54) FRACTURE BRACE

(75) Inventors: David C. Hargrave, Madison, NJ (US);
Eugene Prais, West Milford, NJ (US)

(73) Assignee: DJO, LLC, Vista, CA (US)

( * ) Notice: Subject to any disclaimer, the term of this patent is extended or adjusted under 35 U.S.C. 154(b) by 194 days.

(21) Appl. No.: 11/261,725

(22) Filed: Oct. 27, 2005

(65) Prior Publication Data

US 2007/0100266 A1    May 3, 2007

(51) Int. Cl.
*A61F 5/00*  (2006.01)
*A61F 13/06* (2006.01)
*A61F 13/00* (2006.01)
*A61F 5/37*  (2006.01)
*A61B 19/00* (2006.01)

(52) U.S. Cl.
USPC ............. 602/21; 128/846; 128/869; 128/878; 128/879; 128/881; 602/5; 602/6; 602/13; 602/20; 602/23; 602/61; 602/62; 602/63; 602/64; 602/65

(58) Field of Classification Search
USPC ................ 602/5–6, 13, 20–21, 23, 61–65; 128/878–879, 881
See application file for complete search history.

(56) References Cited

U.S. PATENT DOCUMENTS

| | | | |
|---|---|---|---|
| 4,382,439 A * | 5/1983 | Shen ............................... 602/22 |
| 4,441,490 A | 4/1984 | Nirschl | |
| 4,441,493 A | 4/1984 | Nirschl | |
| 4,654,893 A | 4/1987 | Meyers et al. | |
| 4,662,364 A | 5/1987 | Viegass et al. | |
| 4,788,972 A | 12/1988 | DeBusk | |
| 4,796,611 A | 1/1989 | Wardlaw | |
| 4,881,533 A | 11/1989 | Teurlings | |
| 5,160,314 A | 11/1992 | Peters et al. | |
| 5,254,078 A | 10/1993 | Carter et al. | |
| 5,279,545 A | 1/1994 | Reese, Sr. | |
| 5,383,844 A | 1/1995 | Munoz et al. | |
| 5,399,152 A | 3/1995 | Habermeyer et al. | |
| 5,415,624 A * | 5/1995 | Williams ........................ 602/21 |
| D371,845 S | 7/1996 | Varn | |
| 5,577,998 A | 11/1996 | Johnson, Jr. et al. | |
| 5,672,150 A | 9/1997 | Cox | |
| 5,713,837 A * | 2/1998 | Grim et al. ........................ 602/6 |
| 5,722,092 A | 3/1998 | Borzecki et al. | |
| 5,733,249 A | 3/1998 | Katzin et al. | |
| 5,749,841 A | 5/1998 | Moore | |
| 5,772,620 A | 6/1998 | Szlema et al. | |
| 5,954,676 A * | 9/1999 | Kramer, III ....................... 602/6 |

(Continued)

FOREIGN PATENT DOCUMENTS

FR    1 482 514    6/1966
JP    S58-58042    4/1983

(Continued)

OTHER PUBLICATIONS

European Extended Search Report issued Apr. 9, 2009 in European Application No. 08009539.1.

*Primary Examiner* — Michael Brown
*Assistant Examiner* — Brandon L Jackson
(74) *Attorney, Agent, or Firm* — Ropes & Gray LLP

(57) ABSTRACT

The invention provides, in various embodiments, braces that are capable of stabilizing an injured limb, particularly an injured wrist. An exemplary brace fits across the injury in contact with the user's limb and has an adjustable casing and compressible material.

23 Claims, 31 Drawing Sheets

(56) References Cited

U.S. PATENT DOCUMENTS

| | | |
|---|---|---|
| 6,024,715 A | 2/2000 | Maxwell |
| 6,106,492 A | 8/2000 | Darcey |
| 6,142,966 A | 11/2000 | Hely |
| 6,146,347 A * | 11/2000 | Porrata .................... 602/21 |
| 6,146,348 A * | 11/2000 | Slautterback ............. 602/21 |
| 6,186,966 B1 | 2/2001 | Grim et al. |
| 6,293,918 B1 | 9/2001 | Wang |
| 6,328,706 B1 | 12/2001 | Yattavong |
| 6,443,918 B1 | 9/2002 | Wang |
| D477,088 S | 7/2003 | Brown et al. |
| 6,592,538 B1 | 7/2003 | Hotchkiss et al. |
| 6,692,453 B2 | 2/2004 | Wolfe |
| 6,740,056 B2 | 5/2004 | Slautterback |
| 6,835,182 B2 * | 12/2004 | Darcey ..................... 602/20 |
| 6,866,646 B2 | 3/2005 | Hopkins et al. |
| 6,913,582 B2 | 7/2005 | Chen et al. |
| 7,033,331 B1 * | 4/2006 | Hely ......................... 602/21 |
| 7,048,703 B2 * | 5/2006 | Riach ........................ 602/13 |
| 7,288,076 B2 * | 10/2007 | Grim et al. ................. 602/5 |
| 2002/0002348 A1 | 1/2002 | Wiggins et al. |
| 2003/0139695 A1 * | 7/2003 | Riach ........................ 602/13 |
| 2004/0019306 A1 | 1/2004 | Brewer |
| 2004/0039315 A1 | 2/2004 | Goumas |
| 2004/0049141 A1 | 3/2004 | Slautterack et al. |
| 2004/0092853 A1 * | 5/2004 | Degun et al. .............. 602/27 |
| 2004/0133137 A1 | 7/2004 | Hargis et al. |
| 2004/0143205 A1 | 7/2004 | Ressel |
| 2004/0147862 A1 | 7/2004 | Chen et al. |
| 2004/0176714 A1 | 9/2004 | Darcey |
| 2005/0096575 A1 | 5/2005 | Weaver, II |
| 2005/0197609 A1 | 9/2005 | Mills |
| 2006/0052730 A1 * | 3/2006 | Hargrave et al. ........... 602/5 |

FOREIGN PATENT DOCUMENTS

| | | |
|---|---|---|
| JP | H09-98997 | 4/1997 |
| JP | H10-71163 | 3/1998 |
| WO | WO 97/24085 | 7/1997 |
| WO | WO 2004/078068 | 9/2004 |
| WO | WO-2006/028489 | 3/2006 |

* cited by examiner

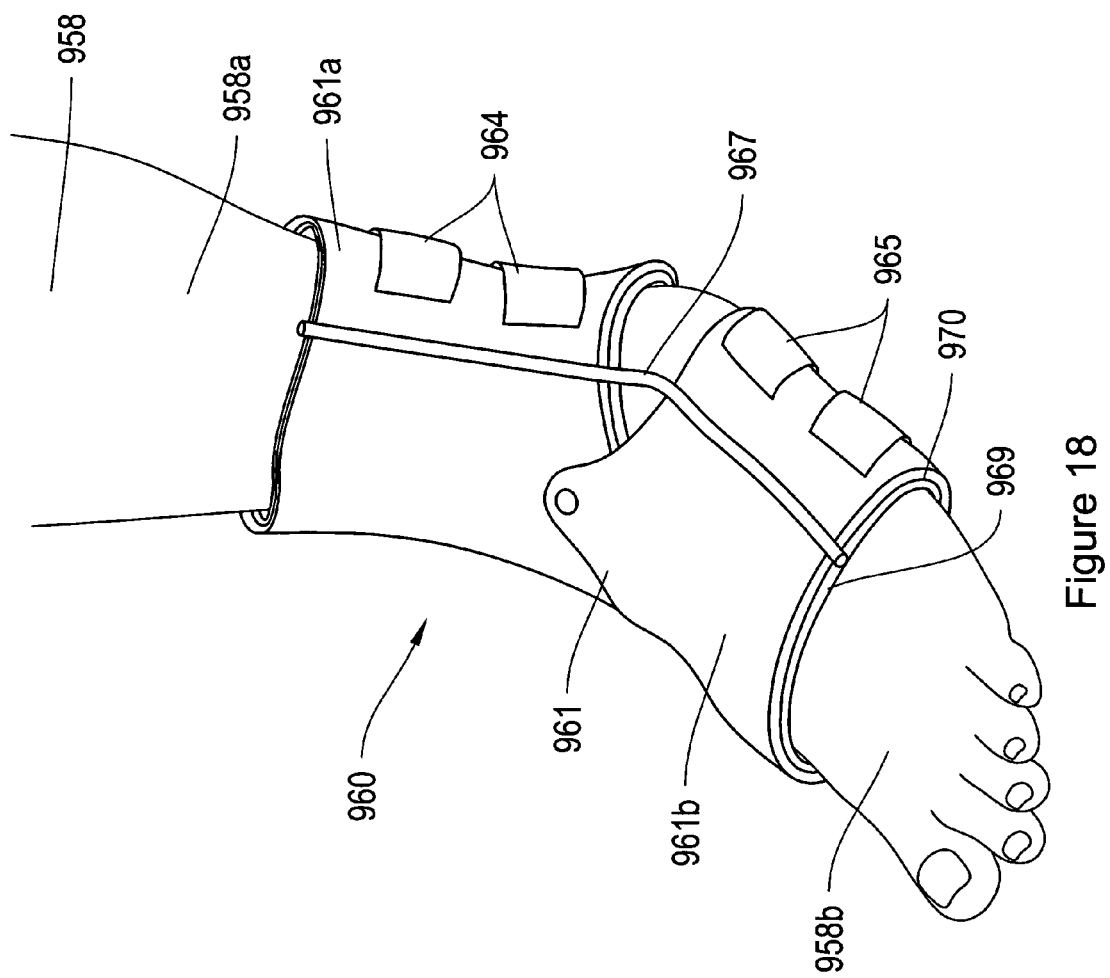

FRACTURE BRACE

RELATED APPLICATIONS

This application is related to U.S. patent application Ser. No. 11/051,791, filed Feb. 3, 2005, the specification of which is incorporated by reference herein.

BACKGROUND

Injuries to the limbs, particularly fractures of the hands, arms and wrist, are commonly treated by the use of a cast or other brace that supports the injured limb and, in certain cases, prevents the limb from rotating around the wrist or other applicable joint. These injuries include sprains, fractures, contusions and other injuries that are common and frequent and, unless properly treated, recurrent.

Certain injuries, particularly limb fractures, result in the limb becoming misaligned with respect to its normal position. This effect may be seen, for example, in an open wrist fracture where radial bones puncture and protrude through the skin and result in the broken radius becoming further bent or otherwise deformed. To treat such a fracture, the physician must appropriately align the fractured limb then apply a support suitable to stabilize the limb during healing. The process of properly aligning and stabilizing a fractured limb to begin healing is known as "reduction" of the fracture. Braces commonly used to maintain reduction of a fracture or otherwise treat an injured limb include plaster casts prepared by a physician and applied by forming the plaster about the patient's limb. In time, the plaster will harden, leaving the limb compressed within a rigid cast. Such braces, although generally effective, cause discomfort and other problems for the patient. For example, a typical compression cast is not adjustable, and therefore its position on the limb is fixed upon compression. This compression may be applied too tightly for some patients; it also may become too loosely attached over time as swelling in the arm recedes.

Thus, it is desirable to have a brace that allows greater flexibility in the function of the brace while still providing adequate support for the injured limb, particularly in the treatment of limb fractures.

SUMMARY OF THE INVENTION

The invention addresses deficiencies in the art by providing, in various embodiments, an adjustable brace that is capable of stabilizing an injured limb, and in a particular embodiment a fractured wrist. The brace is also suitable for treatment of injuries arising from fracture, sprain, contusion, or other injuries to the limb. In certain embodiments the brace fits across and substantially immobilizes the injured limb.

In one aspect, the invention includes a brace for supporting an injured wrist. The brace includes an adjustable casing having a lateral shell and a medial shell and being adapted to impede flexion of the injured wrist, a compressible member at least partially enclosed by the lateral shell, a first mechanical fastener adapted to tighten and loosen the adjustable casing, and a connector assembly adapted to pivotally adjoin the lateral and medial shells. The connector assembly may be a continuously molded connecting membrane, a hinge, a crease, or any other suitable component. One or more of the lateral and medial shells is a stiff shell or, optionally, made of flexible material adapted for patient comfort. The brace may also have a second compressible member at least partially enclosed by the medial shell which may be adapted to fit across the medial side of the user's wrist. The compressible members used with the brace may be made of foam, an inflatable cell, rubber, or suitable compressible material. The mechanical fastener may include any suitable fastener, such as at least one strap connecting the medial and lateral shells.

In another aspect, the invention includes a brace for treating an injured wrist and having a contoured surface fitted to the user's wrist and forearm. The brace has an adjustable casing adapted to impede flexion of the injured wrist and having a lateral shell and a medial shell and a mechanical fastener adapted to tighten and loosen the casing, a first compressible member at least partially enclosed by the lateral shell of the adjustable casing, and a second compressible member at least partially enclosed by the medial shell of the adjustable casing and adapted to form a contoured interface with a region adjacent to the user's thumb on the medial side of the user's hand. In one configuration, the second compressible member of the brace includes a hand region, a wrist region, and a forearm region and wherein the wrist region has a width that is smaller than a width of the hand region and a width of the forearm region. In one implementation, the second compressible member includes a hand region having an interior well adapted to at least partially enclose the user's thumb. The brace may also be configured with a through-aperture in the inner well for receiving the user's thumb.

In a further implementation, the brace is configured to include a compliance monitoring assembly affixed to a portion of the brace and adapted to be disengaged upon disengaging the first mechanical fastener from the brace. The compliance monitoring assembly is provided to allow a physician to identify whether the compliance monitoring assembly has been removed, as evidence of whether the patient has removed or loosened the brace.

These and other features and advantages of the invention are described in further detail below with regard to illustrative embodiments of the invention.

BRIEF DESCRIPTION OF THE DRAWINGS

The foregoing and other objects and advantages of the invention will be appreciated more fully from the following further description thereof, with reference to the accompanying drawings wherein:

FIG. 18 depicts an embodiment of a brace applied to a user's leg.

DESCRIPTION OF CERTAIN ILLUSTRATED EMBODIMENTS

The device and methods described herein provide for braces and methods for bracing an injured limb. To provide an overall understanding of the invention, certain illustrative embodiments are herein described, as more particularly set forth in the figures. However, the systems and methods described herein can be adapted and modified for other suitable applications, and that such other additions and modifications will not depart from the scope hereof.

For example, representative embodiments may be applied to injuries to the forearm, the wrist, hand, fingers, the upper arm, injuries to the leg, or ankle, or to bones of any or all of the foregoing.

Figure 1A:
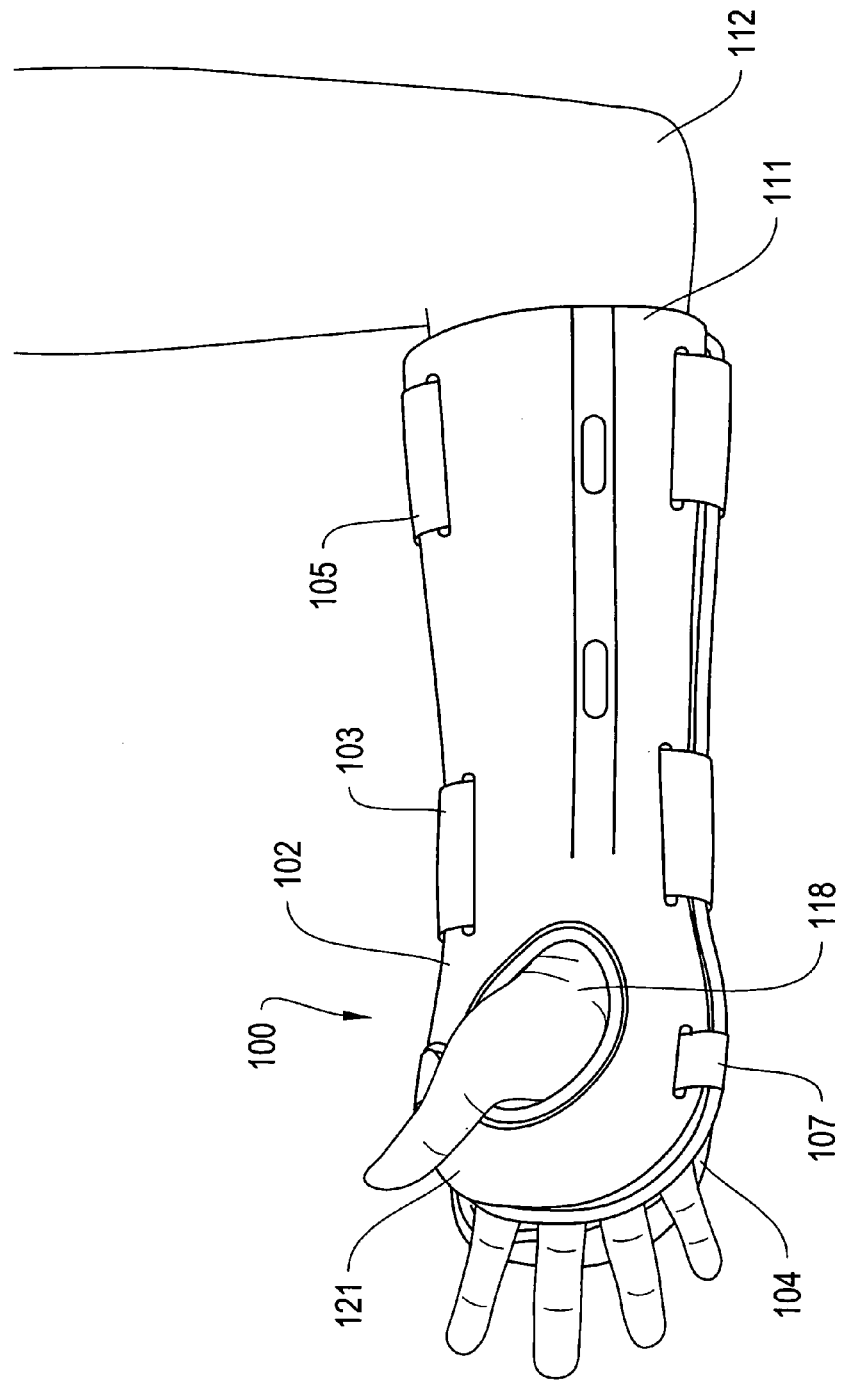
FIGS. 1A-1C depict embodiments of a brace attached to a user's arm.
Figure 1B:
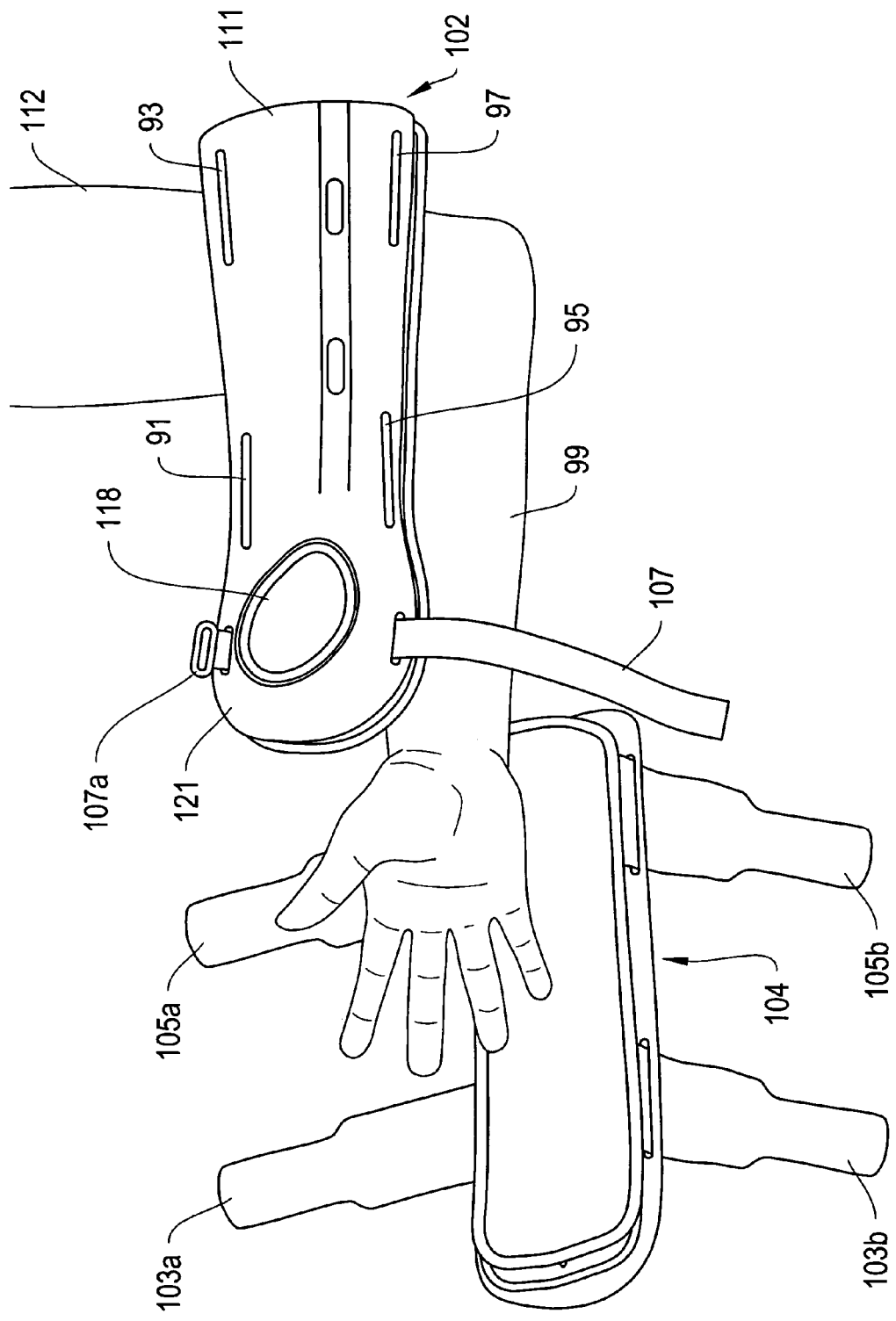

FIGS. 1A-1B depict an embodiment of a brace 100, including a casing 111 having medial 102 and lateral 104 components, the brace 100 being fitted to a patient's limb 112 with medial portion 102 fitted to the volar side 99 of the user's arm and wrist and the lateral portion 104 fitted to the dorsal side (the reverse side of 99, not shown) of the user's arm and wrist. In the depicted embodiment, the medial side 102 of the depicted brace 100 has an extension 121 that surrounds the thumb and supports the fingers of the patient, while the thumb extends through and is supported by a through-aperture 118 surrounded by the extension 121. In practice, the brace 100 is adapted to fit across the injured limb 112 and support a fracture of the limb 112. To this end the brace is secured to the user's limb 112 by adjustable straps, including a mid strap 103, a proximal strap 105, and a distal strap 107.

Figure 2:
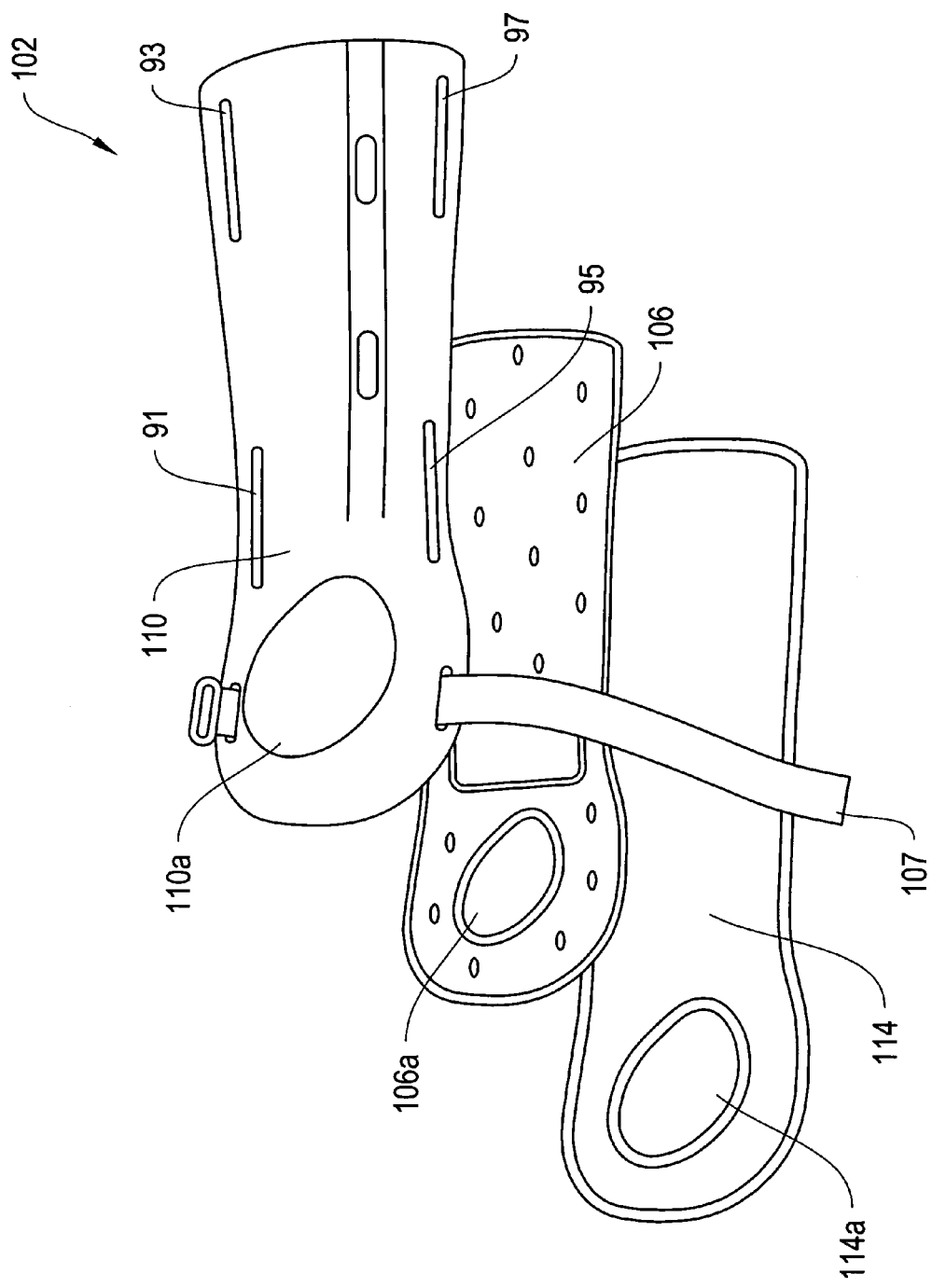
FIG. 2 is an exploded view of a medial casing component of the brace depicted in FIGS. 1A-1C.
Figure 3:
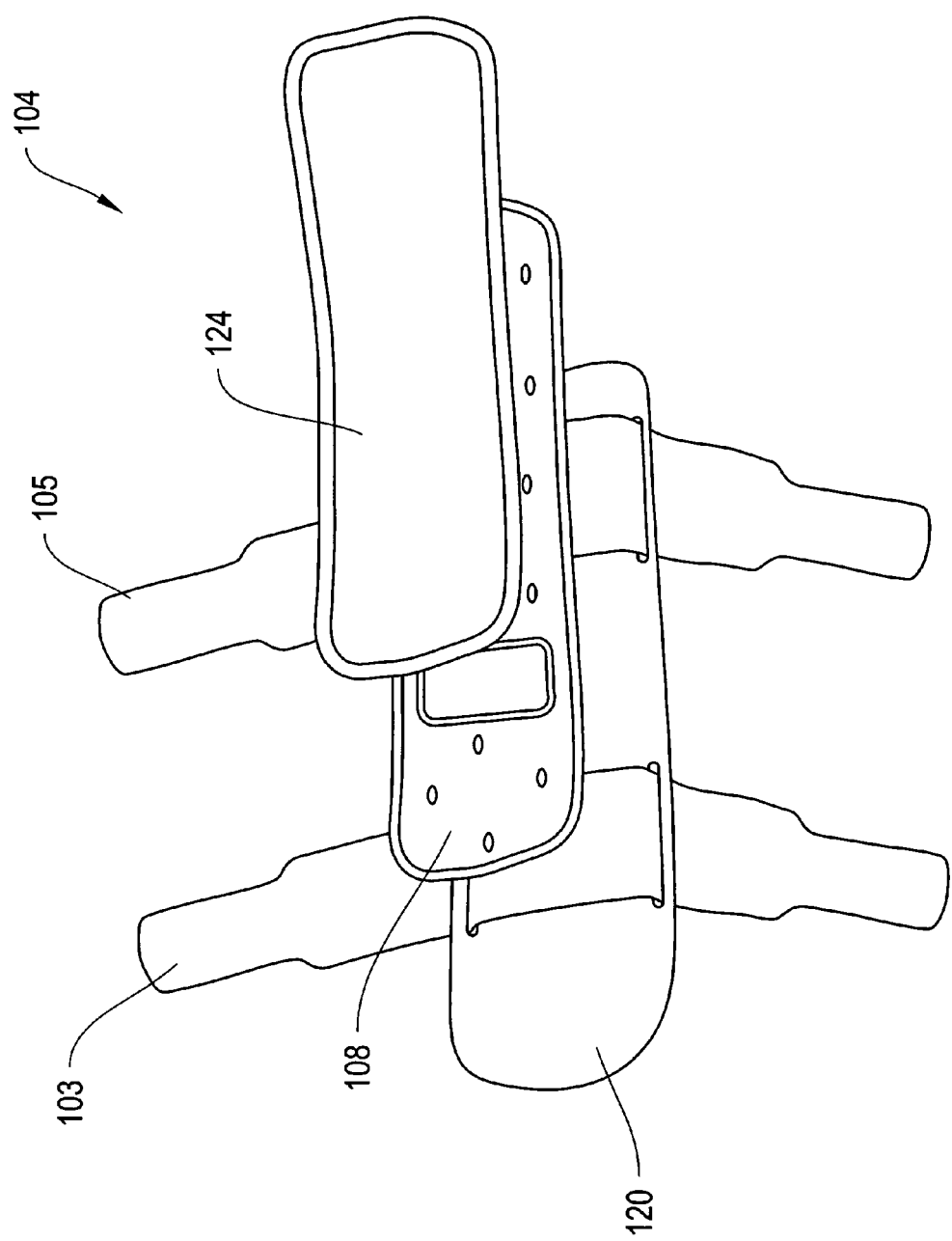
FIG. 3 depicts an exploded view of a lateral casing component of the brace depicted in FIGS. 1A-1C.

The casing 111 has medial 102 and lateral 104 components adapted to provide sufficient support to stabilize a fracture but also sufficiently flexible to provide for patient comfort. FIGS. 2 and 3 are exploded views of the medial 102 (FIG. 2) and lateral 104 (FIG. 3) components of the casing 111 that more particularly describe the medial 102 and lateral 104 casing members. FIG. 2 depicts an exploded view of the medial component 102, which has an outer medial shell 110 and an inner medial liner 114 that, together, enclose a compressible medial member 106. The outer shell 110, inner liner 114 and compressible member 106 each have a through-aperture, 110a, 114a, and 106a respectively, and are fitted together to align such through-apertures to receive the thumb. FIG. 3 depicts an exploded view of the lateral component 104 having an outer lateral shell 120 and inner lateral liner 124 that, together, enclose a compressible lateral member 108.

Figure 1C:
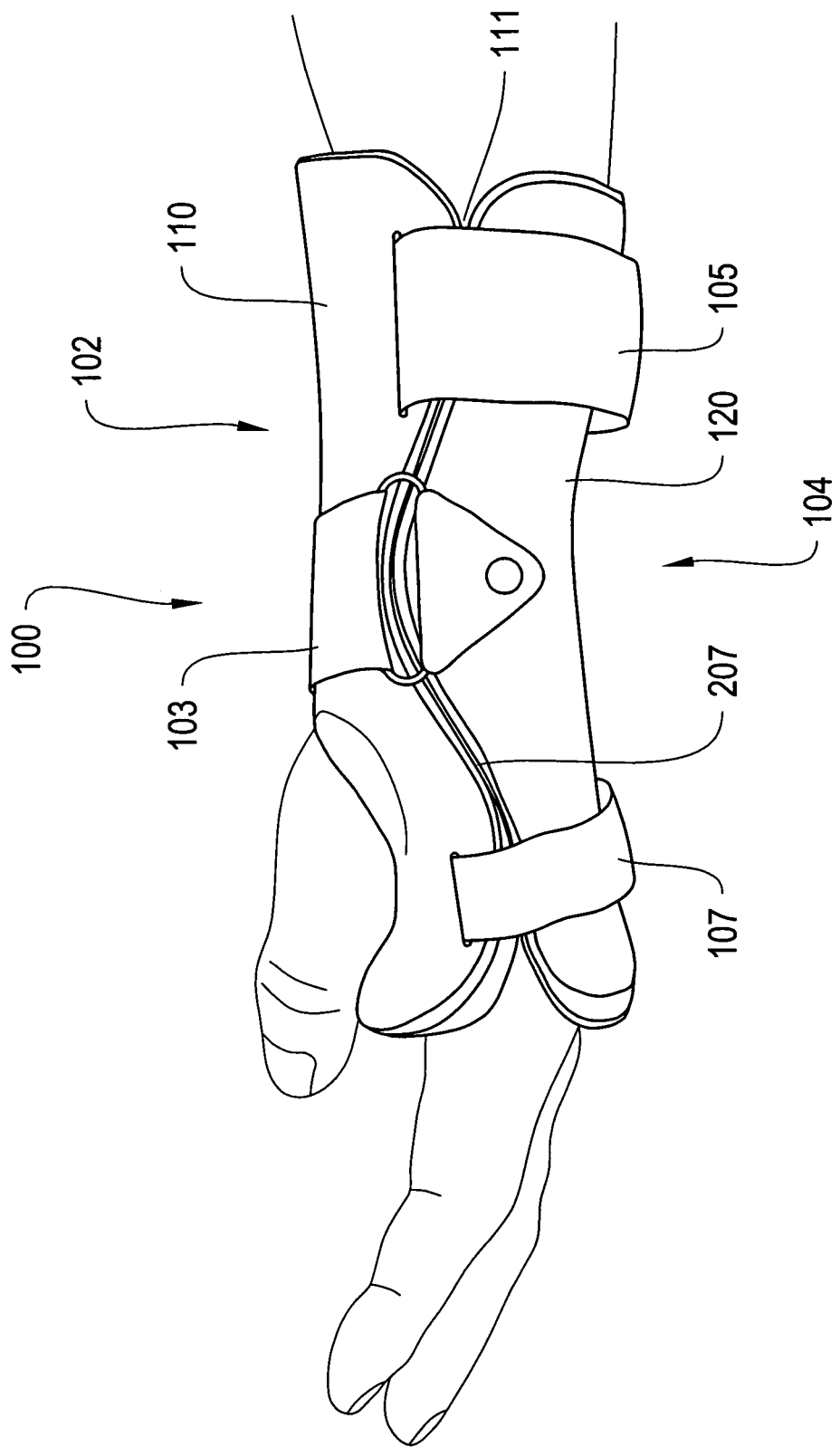

In the depicted embodiment, at least one or both of the outer medial shell 110 and outer lateral shell 120 are rigid, such as a stiff shell. Any suitable stiffening material may be used, such as high density polymer, aluminum, or other stiffening material sufficient to support a fracture. In alternative embodiments, the shells 110 and 120 are constructed of a flexible material, such as low density polyethylene, which allows the brace 100 to conform to the injured limb as the straps 103, 105 and 107 are tightened and yet still support the fracture. As shown in FIG. 1C, a casing 111 made of flexible material may be molded so that the shells 110 and 120 interlock along a seam 207, which allows the medial 110 and lateral 120 shells to envelope the fracture location. Any suitable flexible material may be used that is capable of providing sufficient support for the fracture.

Exemplary flexible materials may include low density polymer, such as low density polyethylene, leather, denim or canvas. In certain embodiments the brace 100 may be constructed from radiolucent material to permit a physician or technician to perform shadowless X-ray on the injury without removal of the brace 100.

The casing 111 may also be configured to have both flexible and stiff components. For example, one or both of the shells 110 and 120 may be flexible in a transverse direction across the limb and may also contain one or more components that stiffen the casing 111 in the dimension longitudinal with the limb.

Flexible casings and flexible casing components allow the casing to be anatomically formed, being adapted to be flexible with respect to the limb and, when tightened, capable of supporting or even immobilizing the limb. In certain embodiments the casing 111 and its components are made of waterproof material for allowing the brace 100 to be submerged in water.

As shown in FIGS. 2 and 3, the compressible members 106 and 108 encompassed by the shells 110 and 120 are positioned to support the volar side 99 and the dorsal side (not shown), respectively, of the arm 112 and support the injury while still maintaining patient comfort. The compressible members 106 and 108 may be constructed of any compressible materials such as inflatable cells or foam pads. Inflatable cells may be adapted to include gel, air, water, or any suitable fluid. Pads may be made of foam, rubber, thick fabric, or any other suitable compressible material. Multiple pads or other compressible material items may be used. The compressible material may be configured to be partially or fully enclosed by the casing 111 when applied to the brace 100.

The compressible members 106 and 108 are shaped, sized, and positioned to provide customized support to selected locations along the limb 112. Such support is also known as "contoured support." FIG. 4 depicts a surface view of a perimeter air cell 500, which is an optional embodiment of compressible material that may be used as compressible member 106 and/or 108, and the cell 500 has a valve 503 for filling and deflating the cell 500.

The depicted air cell 500 has an air compartment 501 with two pockets 504 and 505 interspersed therein, the pockets having inner walls 506 and 507, respectively that separate the pockets from the remainder of the air compartment 501. In this embodiment, air can flow within the compartment 501 but not within the inner pockets 504 and 505. The air cell 500 is sized and shaped for controlling the amount and/or distribution of supporting pressure applied to selected locations on the limb. The air cell 500 contains a valve 503 for adjusting the pressure of one or more air pockets in the air cell 500. An electrical or manual pump not shown may also be employed to adjust the pressure of the air cell 500. In certain embodiments the air pressure of the air cell 500 changes as the user flexes the hand/fingers. Additionally, in certain embodiments, a hand-held pump component not shown may be included with the brace 100 and, when gripped by the user, allows the user to flex the fingers of the user's hand, thereby flexing the muscles in the forearm. Inflation components other than a hand-held pump may be used, such as a ball. The flexing of the forearm may, in turn, provide for a decrease in swelling in the arm. Also known as pulsating pneumatic compression, the process of reducing arm swelling by flexing the forearm may be assisted by this invention, and may help to relieve pain in the patient's arm.

The inner pockets 504 and/or 505 may be inflexible, such as by having an external stiff surface; they may also be stretchable. They may also be separated from the compartment by stitching, gluing, etc. In the depicted embodiment, the inner pockets 504 and/or 505 do not expand significantly when the air cell is inflated. The air cell 500 may be positioned on the limb such that the non-expanding inner pockets 504 and/or 505 form a protective pocket directly above the injury site. In this respect, the compartment 501 may be fitted in contact with the injured limb in the vicinity of the injury site, while leaving the surface immediately above the injury free from contact with the limb. In this embodiment the air cell 500 may be adapted so that supporting air pressure is applied at selected levels and to selected locations such as around the perimeter of the compartment along the limb.

Figure 4:
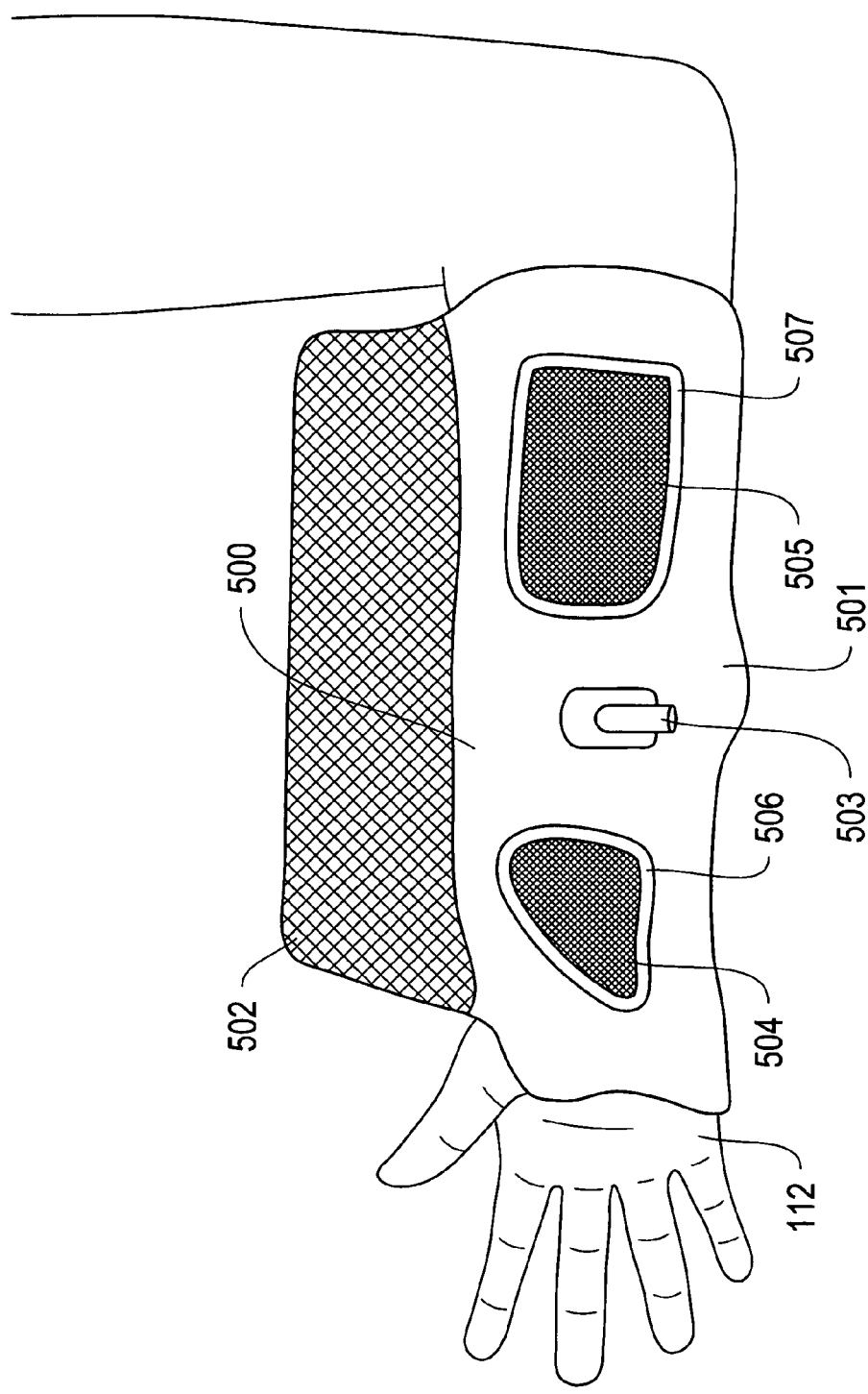
FIG. 4 depicts an embodiment of an exemplary compressible member that may be used with the brace depicted in FIGS. 1A-3.

The compressible material used for the compressible members 106 and 108, such as the air cell 500 depicted in FIG. 4, may be quilted, dimpled, or otherwise adapted to provide compartmental air pockets with reduced or no fluid communication there between. Air cells with compartmentalized air pockets may be configured to be less expandable than pockets with little or no compartmentalization, and compartmentalizing the pockets provides the user with the ability to control the pressure and/or distribution of the air cell at given points along the limb.

The compressible material, such as an air cell of the type manufactured and sold by the Aircast LLC of Summit, N.J., has one or more surfaces or compartments adapted to contact the injured limb, such as in the vicinity of the fracture or other injury, and apply a desired supporting pressure to the limb while certain surfaces or compartments of the material do not contact the limb. While an air cell 500 is exemplified in FIG. 4, foam pads or other suitable compressible material may be adapted to provide contoured support to the injured limb. In certain embodiments, compressible members 106 and/or 108 may have varied thickness along the material, providing one or more sections that contact the injured limb and one or more sections that have no or little contact therewith. In certain embodiments the compressible material may be adapted to provide pillow-like support under a fracture or other injury site on the limb. Examples of inflatable cells that may be used as compressible members are found in U.S. patent application Ser. No. 10/726,343 (entitled "Orthopedic Appliance with Moisture Management System" by Johnson et al.). Other examples are found in U.S. Pat. No. 6,755,798 (by McCarthy and Hargrave).

In certain embodiments, the compressible members 106 and/or 108 have multiple compartments that provide balanced support of an injury along the outer edges of the compressible member, thereby impeding the cell 500 from inflating like a football, a condition that would result in the center of the cell 500 being relatively thick and tapering to the sides thereof, which would allow applied external forces to displace the air to the center of the brace 100 and provide less support for the injury than is provided by multi-compartment air cells.

With continued reference to FIGS. 2 and 3, the brace 100 includes liners 114 and 124 positioned within the medial 102 and lateral 104 components of the casing 111. The liners 114 and 124 are positioned between the user's arm and their respective casing components 102 and 104. The liners 114 and 124 are adapted to absorb moisture from the limb 112. In certain embodiments the liner is fabric e.g., a wicking material, perforated foam, or it may be any other suitable material. The liners 114 and 124 contact the limb and may assist in fitting the casing 111 to the limb. The liner may be positioned in any position for example, adjacent to the user's arm to achieve desired comfort and effect.

As described more fully below with reference to FIGS. 11A-11D and 15, the air cell 500 may also be adapted to facilitate ventilation and moisture management. For example, the cell 500 may have holes that allow ambient air or cooling agents to contact the arm. In alternative embodiments, the brace may include a bladder filled with liquid e.g., cold water. Suitable heat-transfer materials e.g., aluminum may also be used to form at least a part of the brace and thereby facilitate the ventilation and/or cooling of the arm. In certain embodiments, the brace is adapted to allow the patient to be treated by cryotherapy, preferably without removing the brace.

With continued reference to FIGS. 1A and 1B, the brace is configured to be adjustable by the use of straps 103, 105 and 107, thereby allowing the user to tighten the brace 100 as necessary to achieve desired support. The mid- and proximal straps 103 and 105 are fitted to the brace 100. In particular, the upper end 103a of strap 103 is fitted through slot 91, and the lower end 103b of strap 103 is fitted through the slot 95. The strap ends 103a and 103b are configured with a Velcro or other connecting mechanism, such that after fitting through their respective slots 91 and 95 the strap ends 103a and 103b are wrapped back upon themselves in a Velcro or other suitable connection fixed along the dorsal side (not shown) of the brace 100. The proximal strap 105 is similarly fitted to the brace 100 by sliding its ends 105a and 105b through slots 93 and 97, respectively, then attaching in a Velcro or other suitable connection along the dorsal side (not shown) of the brace 100. The distal strap 107 fits under the distal end of the brace 100 through a through-aperture (not shown) and is secured on the dorsal side by buckle 107a. While straps are depicted in the exemplary embodiment, the casing 111 may also contain buckles, laces, or other suitable mechanical structures for this purpose. The straps may be of flexible elastic or non-elastic material. The straps or other suitable structure may assist in stabilizing or even immobilizing the injured limb.

Furthermore, the straps 103, 105 and 107 allow the brace 100 to be adjusted and removed and re-attached as desired by the patient or physician. In one aspect, the straps 103, 105 and 107 enable the user to tighten the casing 111 during its initial placement on the arm 112 as necessary to support the injury, while avoiding over-compression that often results when a common plaster cast is used. In another aspect, the adjustability feature may assist in managing swelling in the vicinity of an injury. As swelling recedes during the course of healing, the adjustable casing 111 allows the user to tighten the brace 100 in response, thereby further pushing swelling fluid away from the site of the injury and toward the center of the user's torso. This process is known as "milking the edema." In another aspect, the straps 103, 105 and 107 allow brace 100 to be removed by the user to expose the injured arm 112 for a physician check-up, for taking X-rays, or any other reason, and it may be placed again on the injured arm when desired.

As noted above, the casing 111 includes at least one component, such as extension 121 on the medial component 102, that extends across the wrist from the forearm to the hand and is adapted to impede the wrist from undergoing one or more of palmer flexion, dorsal flexion, radial deviation, and ulnar deviation, and optionally also to impede the pronation and supination of the forearm. Impeding one or more of such motions may include impeding the wrist or forearm from extending in the range of motion enabled by such rotation. In certain embodiments, the brace 100 includes at least one component positioned against the arm and hand so as to impede dorsi flexion, palmar flexion, ulnar deviation and radial deviation of the wrist, without impeding pronation or supination of the forearm. In certain embodiments the brace 100 may have one or more components adapted to impede palmar and dorsi inflection of a wrist but not radial or ulnar deviation, or to impede radial and ulnar deviation but not palmar or dorsi inflection.

The depicted brace is capable of stabilizing the injured arm, particularly an injured wrist, and, in certain embodiments, the brace may immobilize the hand, wrist, fingers, thumb, or any of the foregoing. To this end, the brace may be adapted to impede rotation of the wrist to stabilize a fracture or a sprain. Those skilled in the art recognize, however, that the brace may also be suitable for use to stabilize an arm suffering from carpal tunnel syndrome or from ligament or tendon injuries. In certain embodiments, the brace is adapted to immobilize the wrist, such as by prohibiting rotation of the hand around the wrist joint, and may optionally be adopted to prevent flexing in the fingers and thumb. The brace may immobilize the wrist against palmar flexion, dorsi flexion, radial deviation, and ulnar deviation, and may also immobilize the pronation and supination of the forearm. The brace 100 may, but need not, be adapted to impede the extension and flexion of the arm about the elbow or about the shoulder. The brace may also be adapted as an ankle brace to impede the flexion, deviation, inversion or eversion of an ankle. An ankle brace may have at least one component e.g., the adjustable casing, a rod or other stiff item, etc. that allows the brace to impede plantar flexion, dorsal flexion, inversion, and/or eversion of the ankle.

Figure 5:
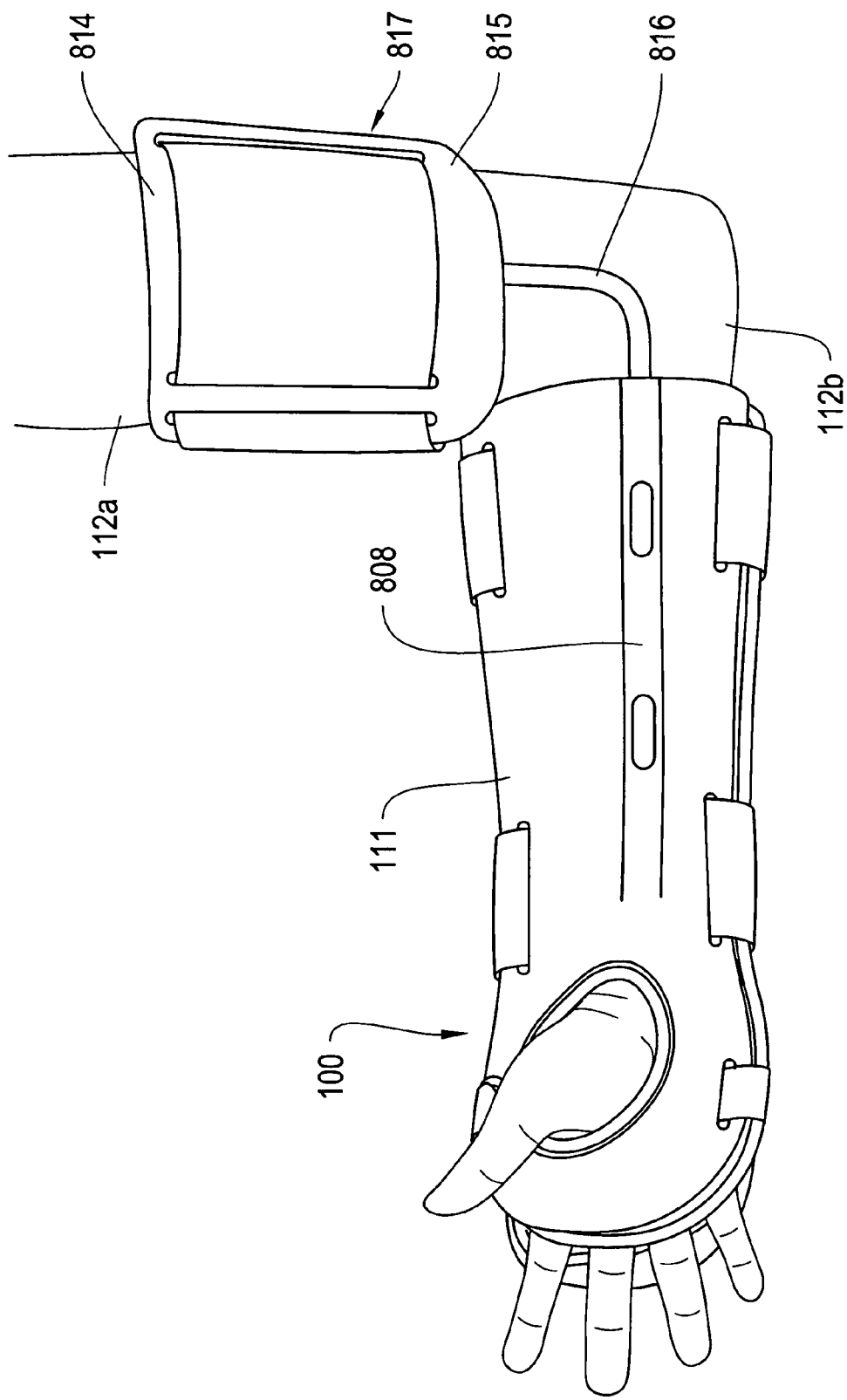
FIG. 5 depicts an alternative embodiment of a brace configured to have a removable arm support for stiffening the brace.
Figure 6:
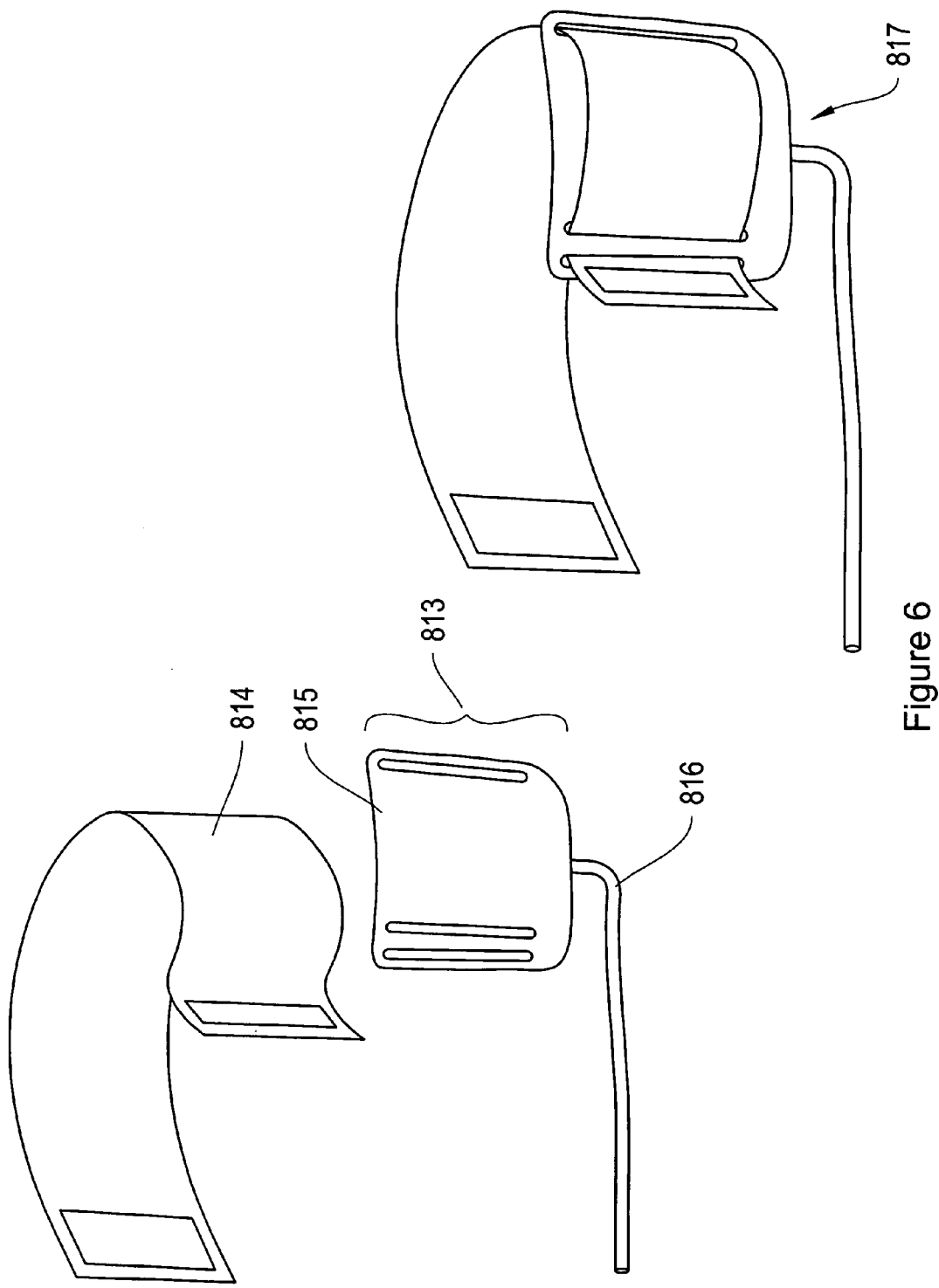
FIG. 6 depicts a close-up view of the arm support applied in FIG. 5.

The brace 100 and accompanying components may also be adopted and modified in additional configurations to provide the desired support for an injured limb. In one such exemplary alternative modification, the brace 100 is used with ancillary stiffening and strengthening components for use in stabilizing the patient's limb. One such configuration is shown in FIGS. 5 and 6. As shown, the brace 100 includes a removable support 817 for connecting one portion of a user's arm 812*a* to another portion 812*b* and thereby impeding the forearm 112 from undergoing pronation and supination. The support 817 may be removable and includes a bracket 813 having plate 815 and rod 816 portions that are secured to the user's upper arm 112*a* by an arm band 814. The depicted embodiment shows the bracket rod 816 affixed to the casing 111 by a slot 808 formed in the casing 111, and extending proximally up the user's arm 112 and into the plate 815. The slot 808 and bracket 813 are adapted to allow the user to adjust and stabilize the angle between the upper arm and the forearm. The angle may be 90 degrees or any other desired angle. The support or any component thereof may be adjustable in length. In certain embodiments the support may be attached and removed by the user. In other alternative modifications the brace 100 includes a rod applied across an injured limb so as to fasten to a user's forearm and to the user's hand, to impede flexion, deviation, etc. without impeding the flexibility of the thumb.

Figure 7:
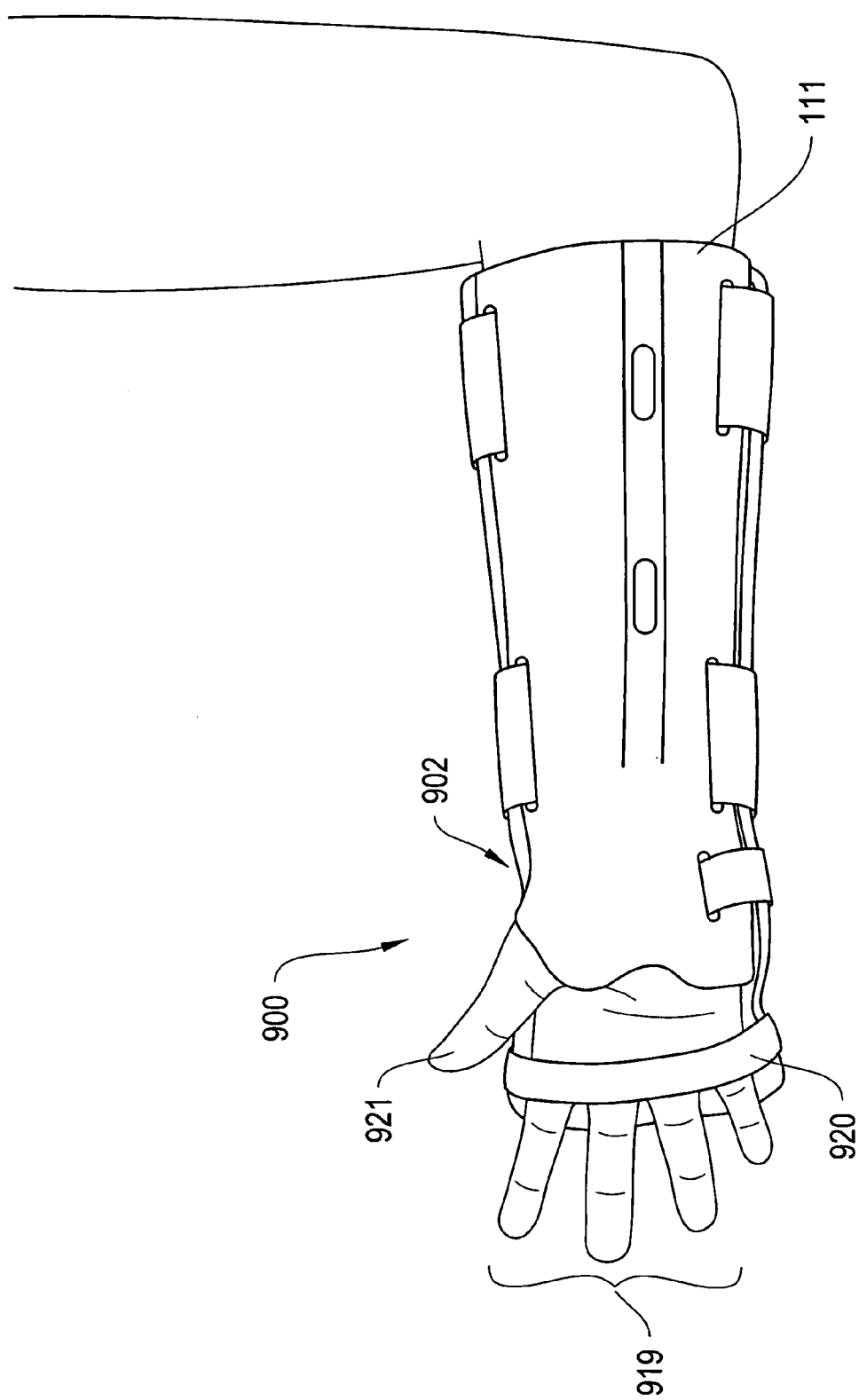
FIG. 7 depicts an alternative embodiment of a brace, the brace having a finger strap.
Figure 8:
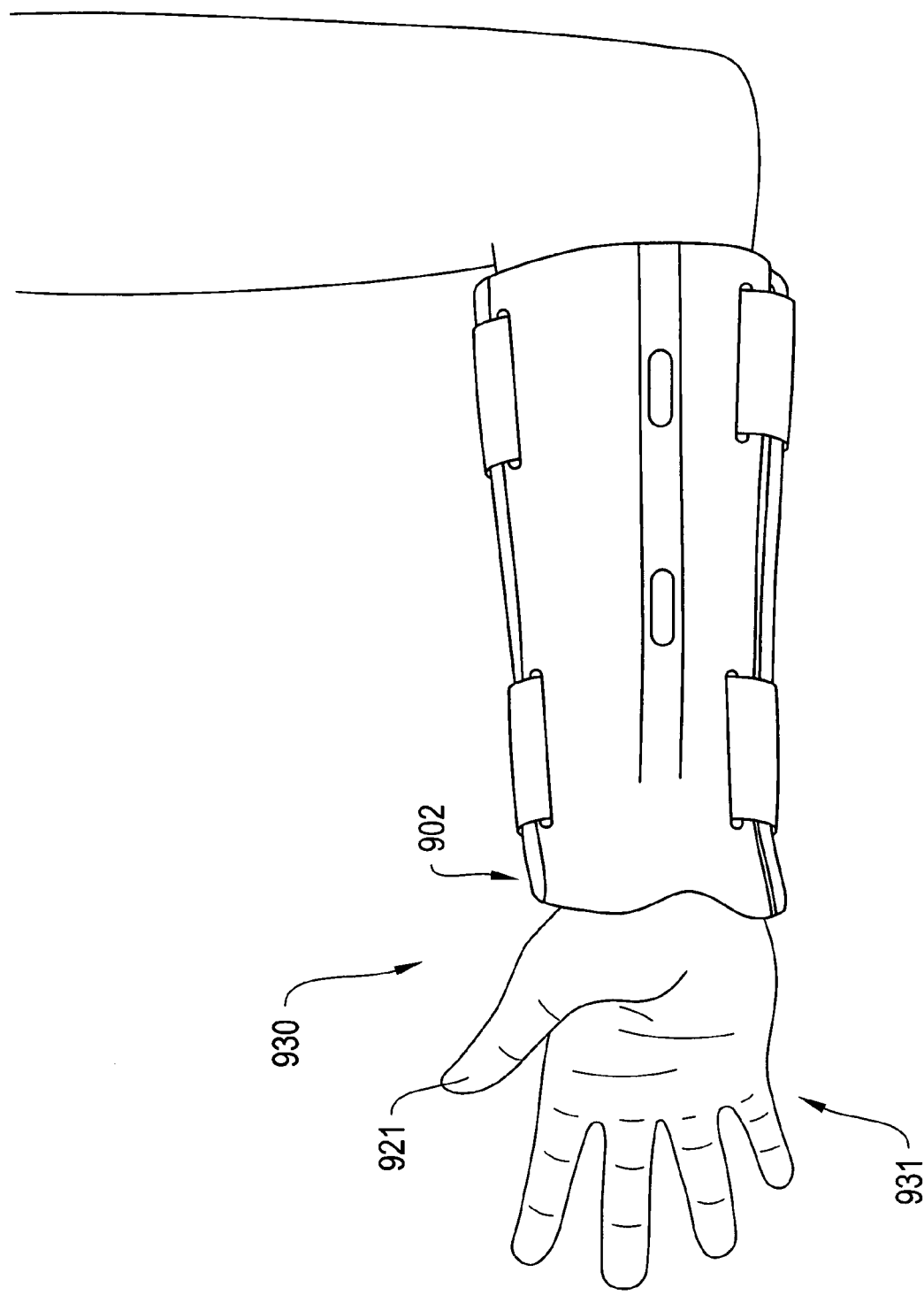
FIG. 8 depicts an alternative embodiment of a brace having an extension on the medial casing adapted to extend into contact with a user's hand.
Figure 9:
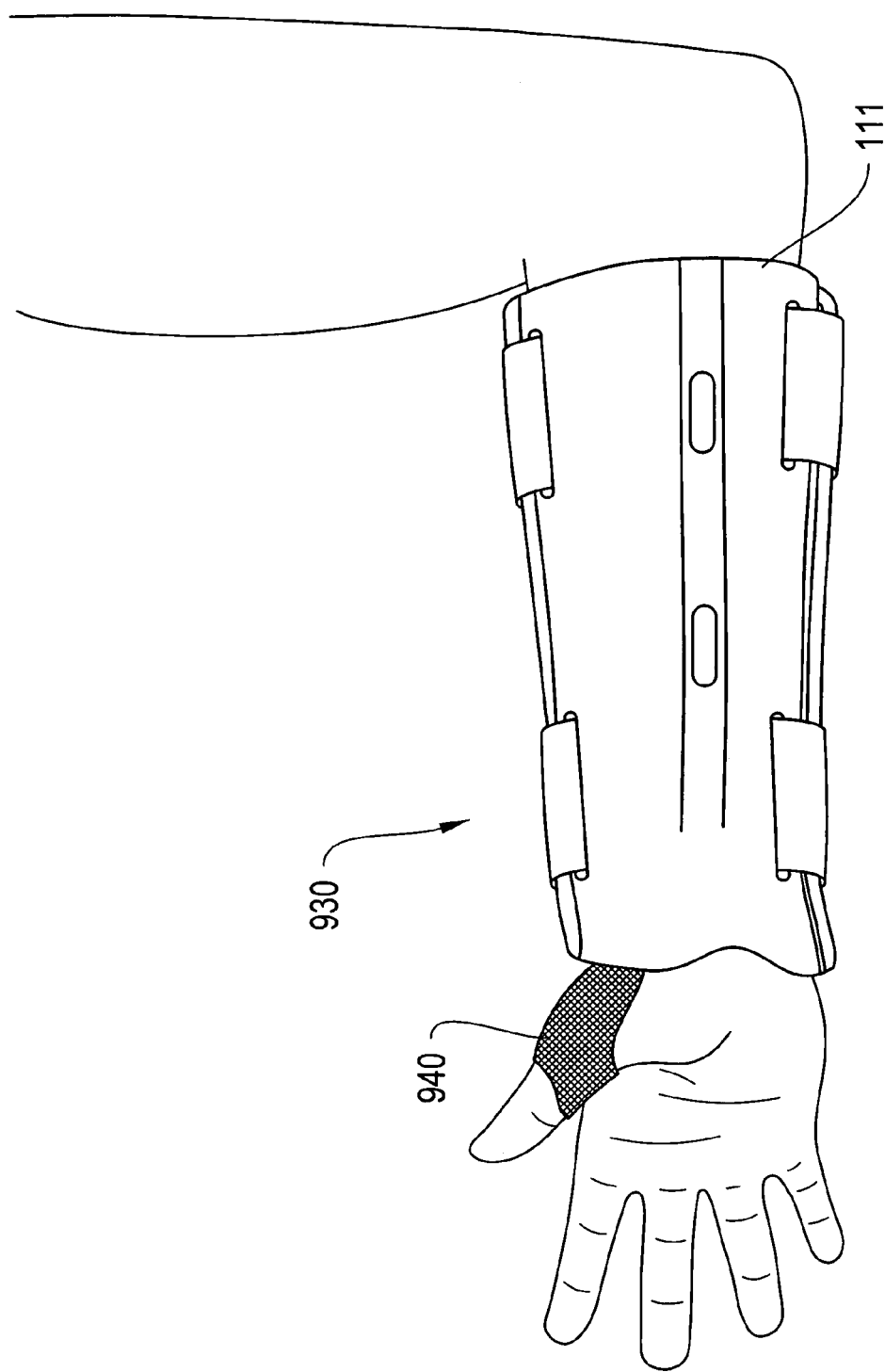
FIG. 9 depicts an alternative embodiment of a brace with a spica for stabilizing the thumb.
Figure 10:
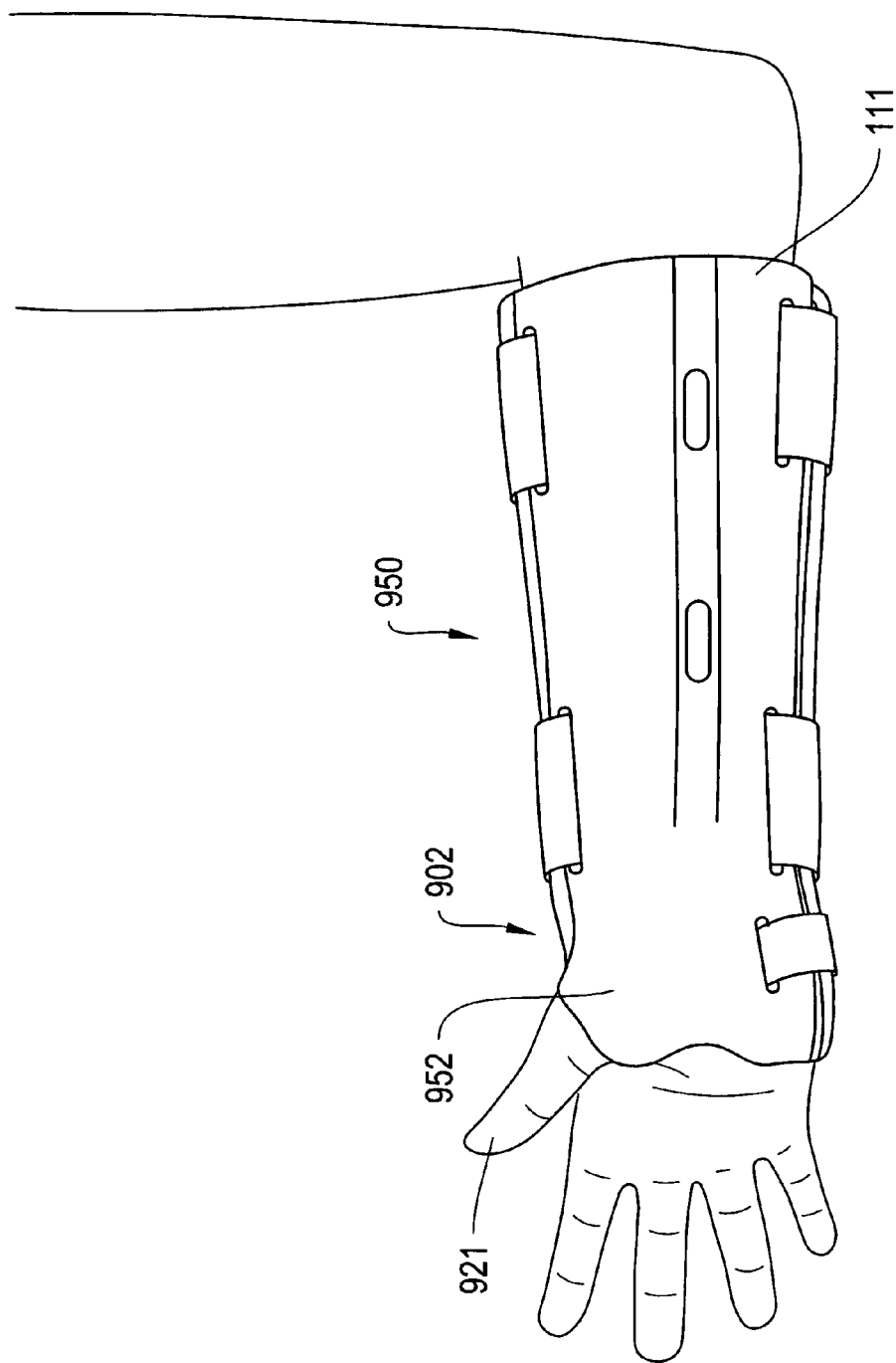
FIG. 10 depict an embodiment of a brace having an extension on the medial casing adapted to extend into contact with a user's hand.

In other alternative modifications, the brace 100 is configured to allow the user's thumb to continue to flex while still supporting the limb. FIG. 7 depicts a medial side view of an example of such an alternative configuration of a brace 900. The brace 900 is similar to brace 100 in that part of its casing 111 extends above the wrist 902 into contact with the thumb 921 without encircling the thumb 921. The brace 900 also has a lateral side that extends to a position above the back knuckles of the fingers 919, such extension serving to impede the rotation of the wrist 902, and further includes a strap 920 to support the hand against the lateral portion of the brace to further impede the rotation of the wrist 902. FIG. 8 depicts another example, showing a brace 930 from the view of the medial side thereof and being adapted to support a fracture without encircling the thumb 921. The depicted brace includes an extension portion that extends above the wrist 902 into contact with the hand 931, such extension serving to impede the rotation of the wrist 902, without encircling the thumb 921 or contacting the knuckles of the fingers on the lateral side of the brace (not shown). FIG. 9 depicts an alternative configuration of the brace 930 with the added feature of a spica 940 connected to the casing 111 to further support the thumb. FIG. 10 depicts another embodiment of a brace 950 from a medial side view having an extension 952 similar to extension 121 on brace 100 except that the extension 952 extends above the wrist 902 into contact with the thumb 921 without encircling the thumb, such extension serving to impede the rotation of the wrist 902 while still allowing the thumb 921 to flex.

In other alternative modifications, the brace 100 is configured to provide contoured support to the user's limb. The contoured support of the brace is achieved by configuring the compressible members used with one or both of the medial 102 and lateral 104 components. FIGS. 11A-D depict ulnar, volar, dorsal and interior views, respectively, of a right-arm wrist brace 130 providing contoured support for the user's wrist according to one alternative embodiment of the invention. The brace 130 includes an adjustable casing 111 having a medial housing assembly 132, a lateral housing assembly 138 and proximal 139, middle 141, and distal 143 straps, similar to the casing 111 with its medial 102 and lateral 104 components and straps 103, 105 and 107 described above.

Figure 11A:
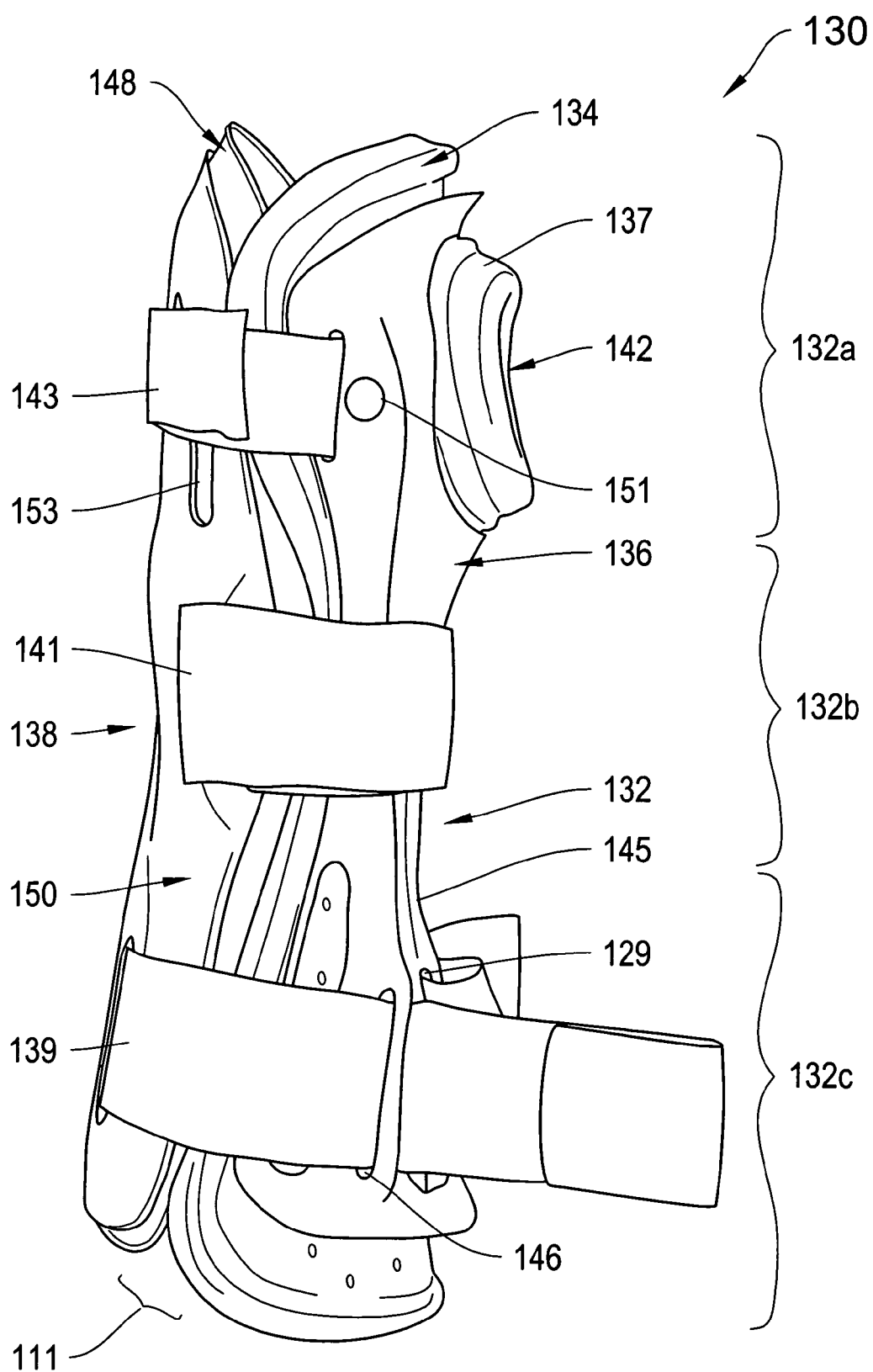
FIGS. 11A-11D depict an alternative embodiment of a brace according to the invention.
Figure 11B:
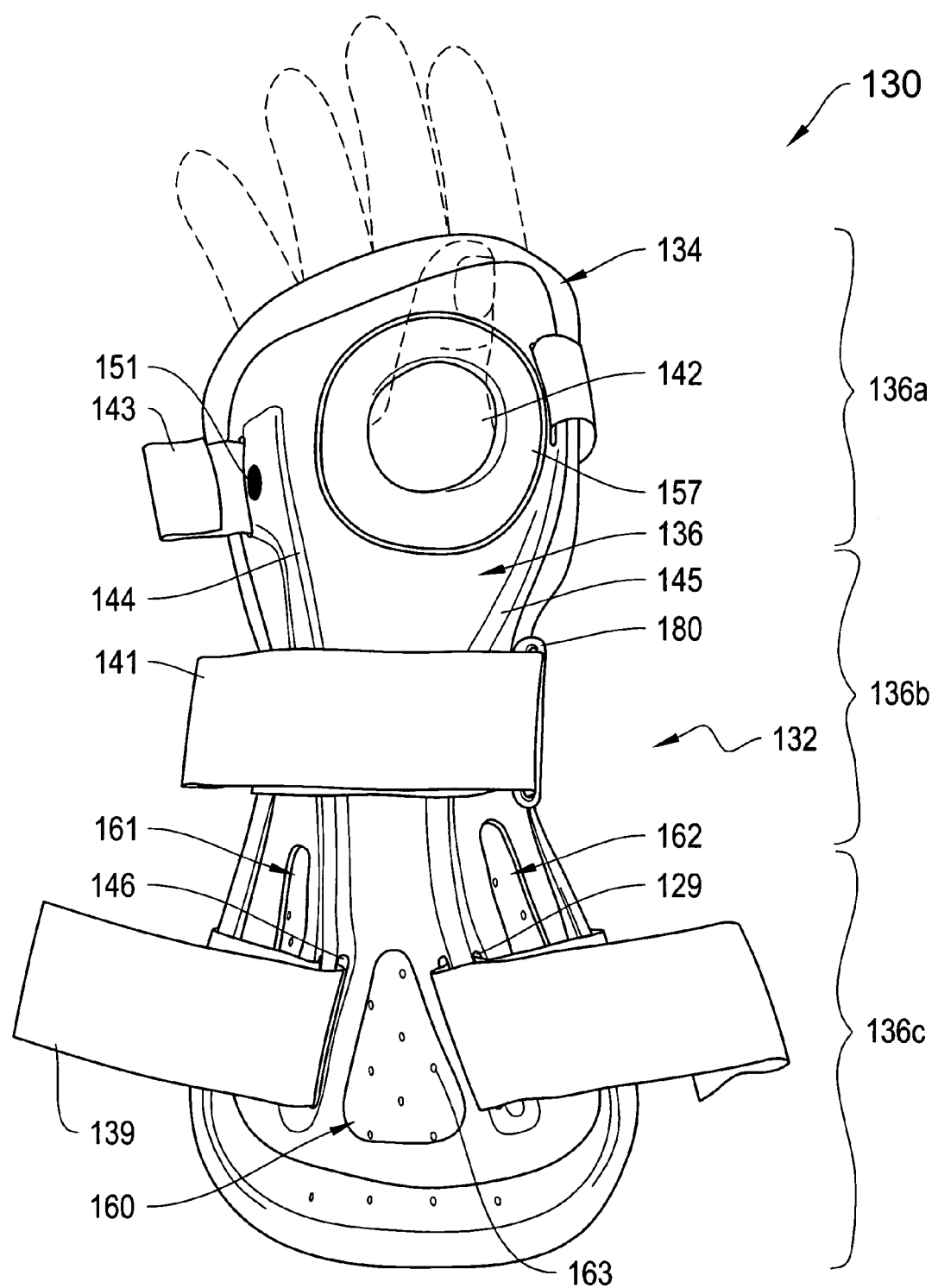
Figure 11C:
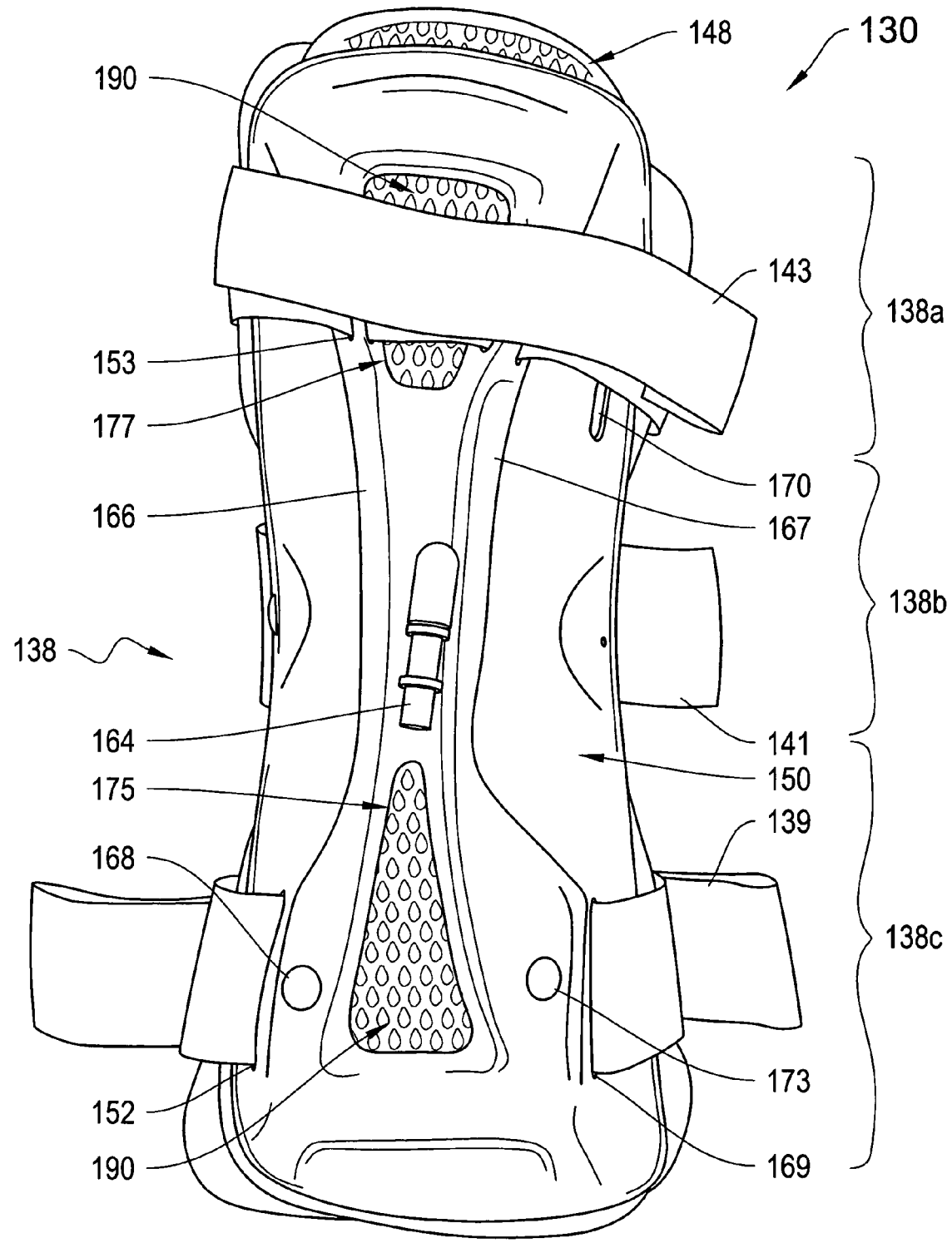
Figure 11D:
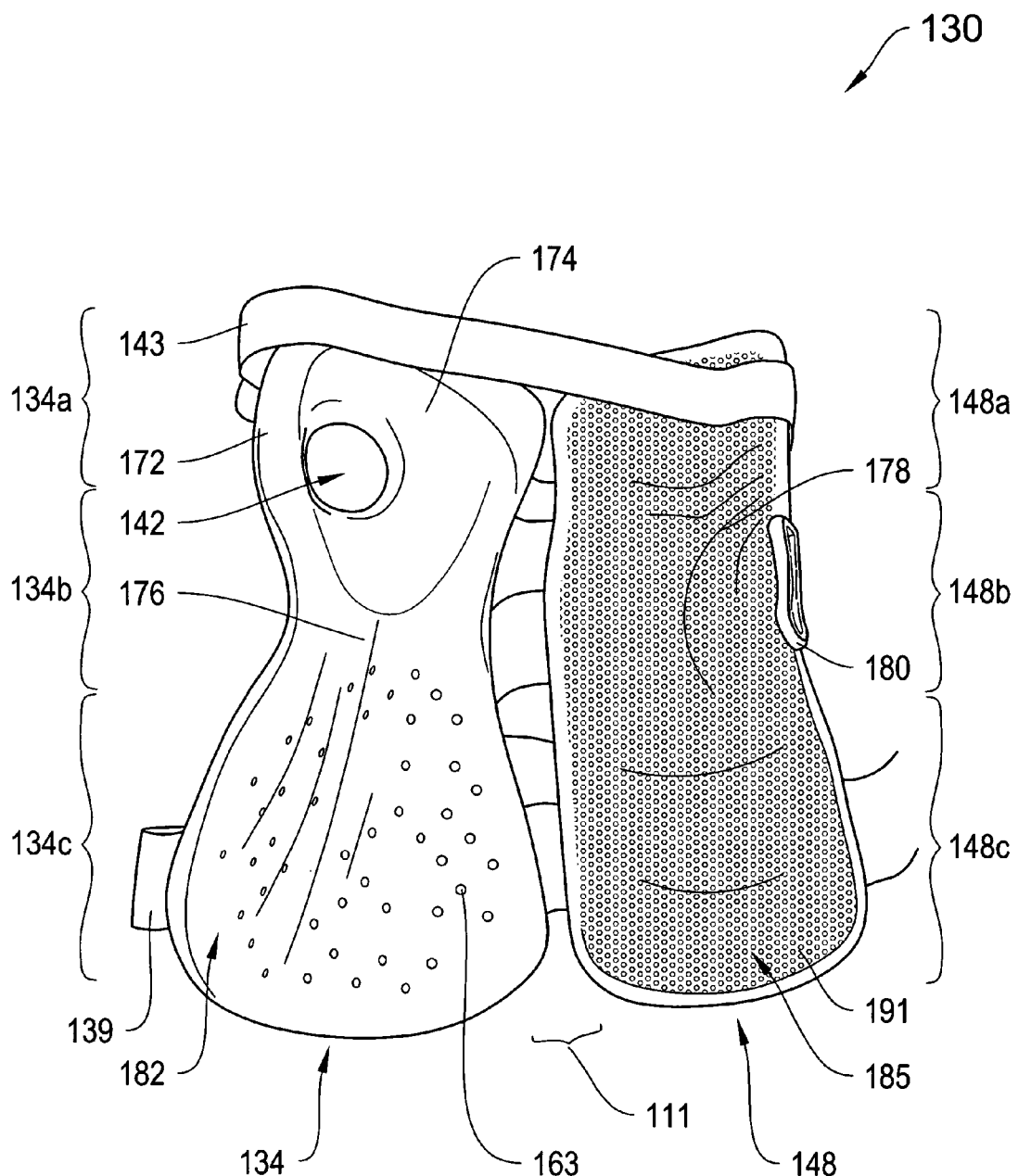

As shown in FIGS. 11A, 11B, and 11D, the medial housing assembly 132 includes an outer medial shell 136, an inner support pad 134, and a through-aperture 142 positioned within the inner support pad 134. According to one feature, the medial housing assembly 136 is contoured to fit over the volar side of a patient's right hand, wrist, and forearm, such that when the brace 130 is placed on the right forearm of the patient, the patient's right thumb extends through the aperture 142 which supports the user's thumb. The medial housing assembly 132 includes a distal section 132*a* sized to enclose a patient's hand and including the aperture 142 for the patient's thumb, a tapered middle section 132*b* for placement of a patient's wrist, and an enlarged proximal section 132*c* sized and shaped to fit around the patient's forearm.

Figure 12A:
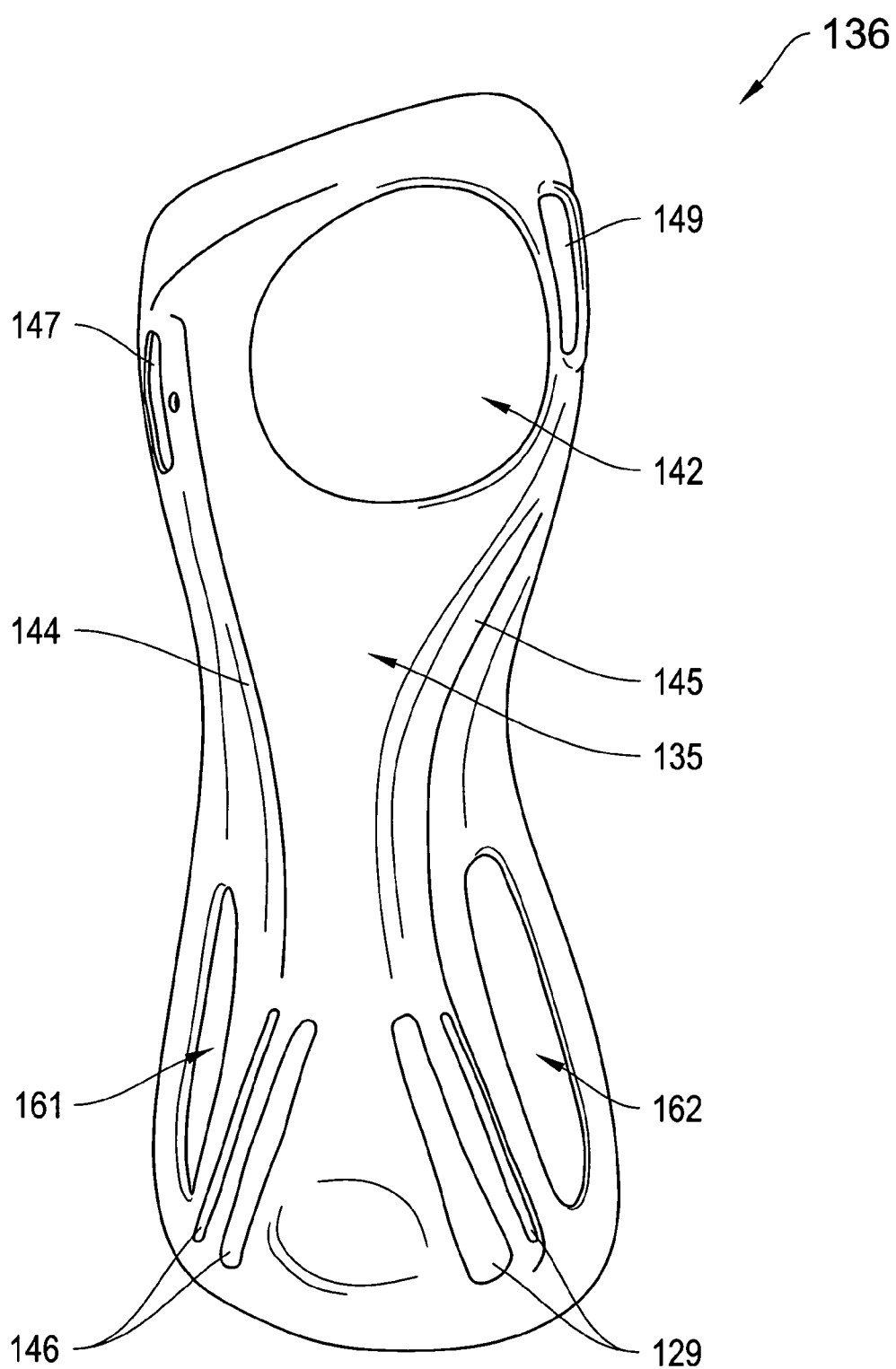
FIGS. 12A-12C depict an exemplary medial outer shell used with the brace depicted in FIGS. 11A-11D.
Figure 12B:
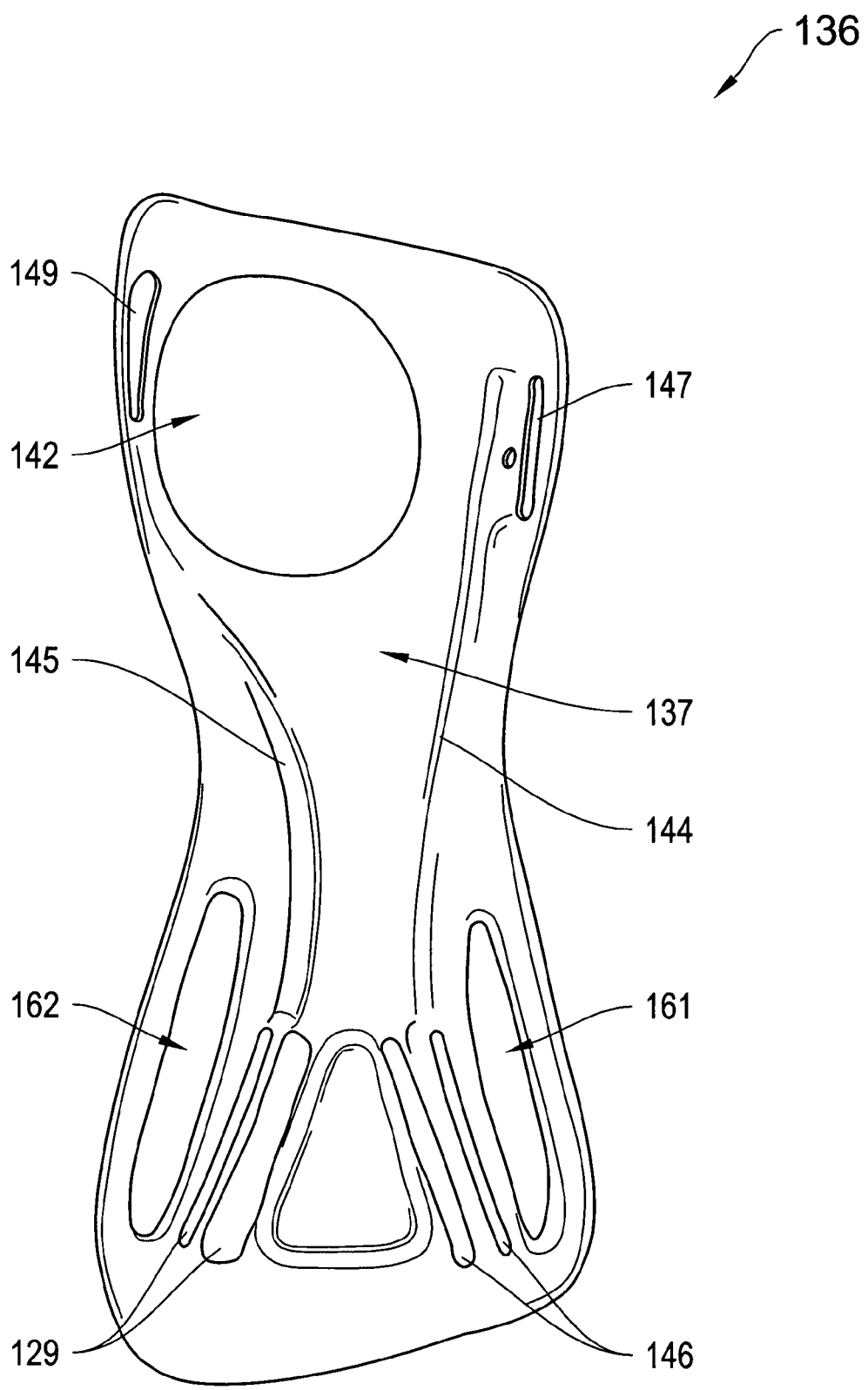
Figure 12C:
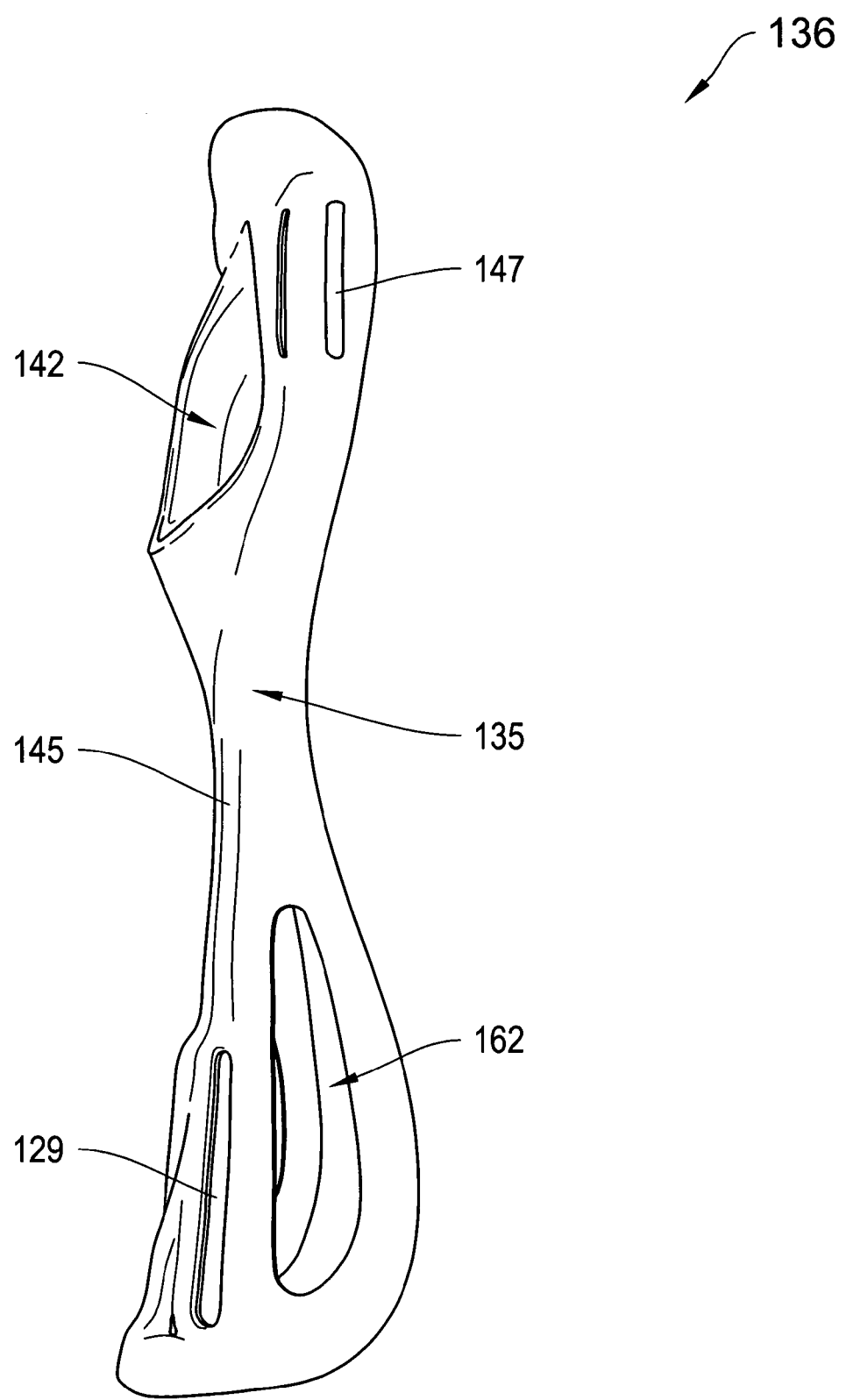
Figure 13A:
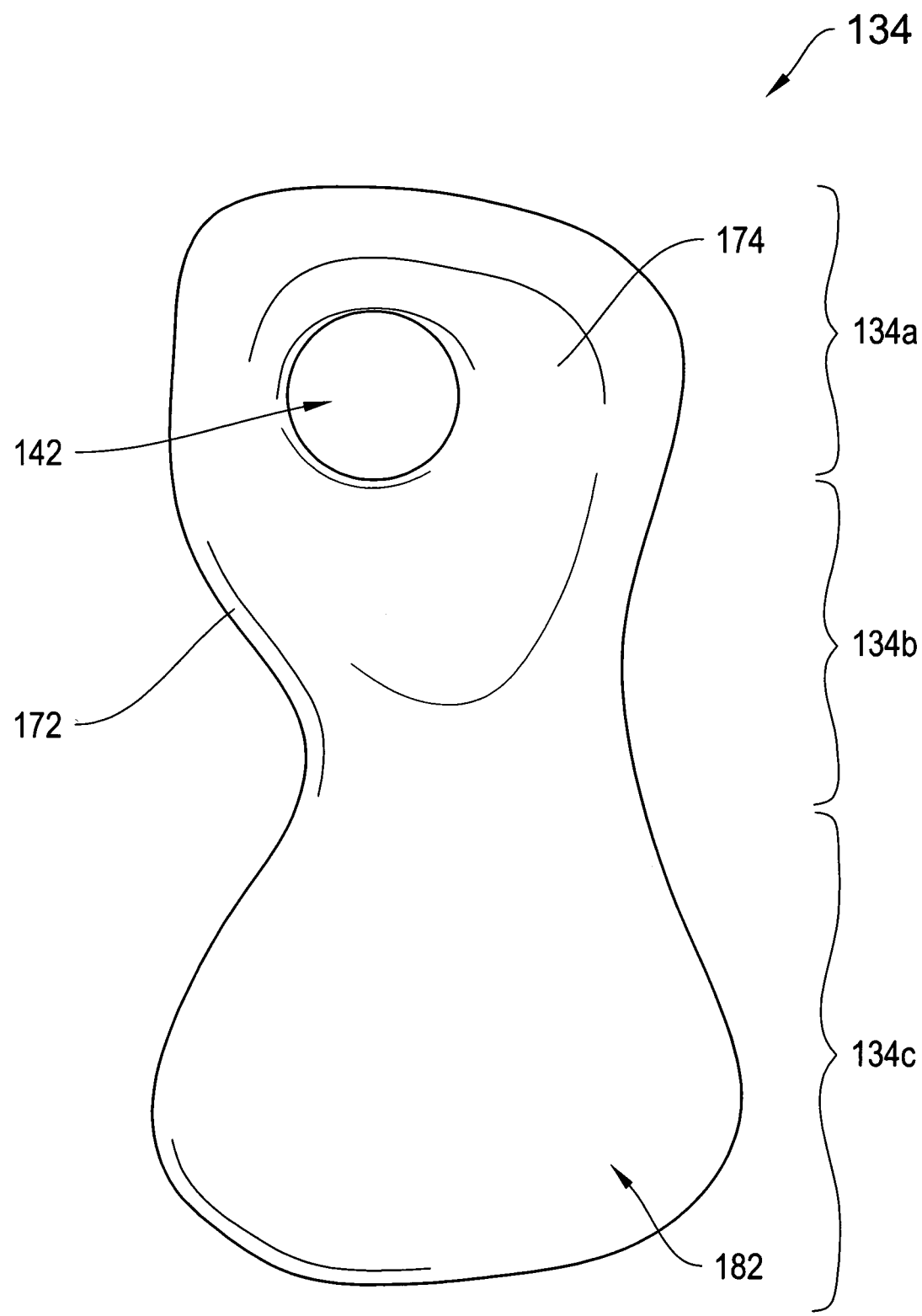
FIGS. 13A-13D depict an exemplary medial inner support member used with the brace depicted in FIGS. 11A-11C.
Figure 13B:
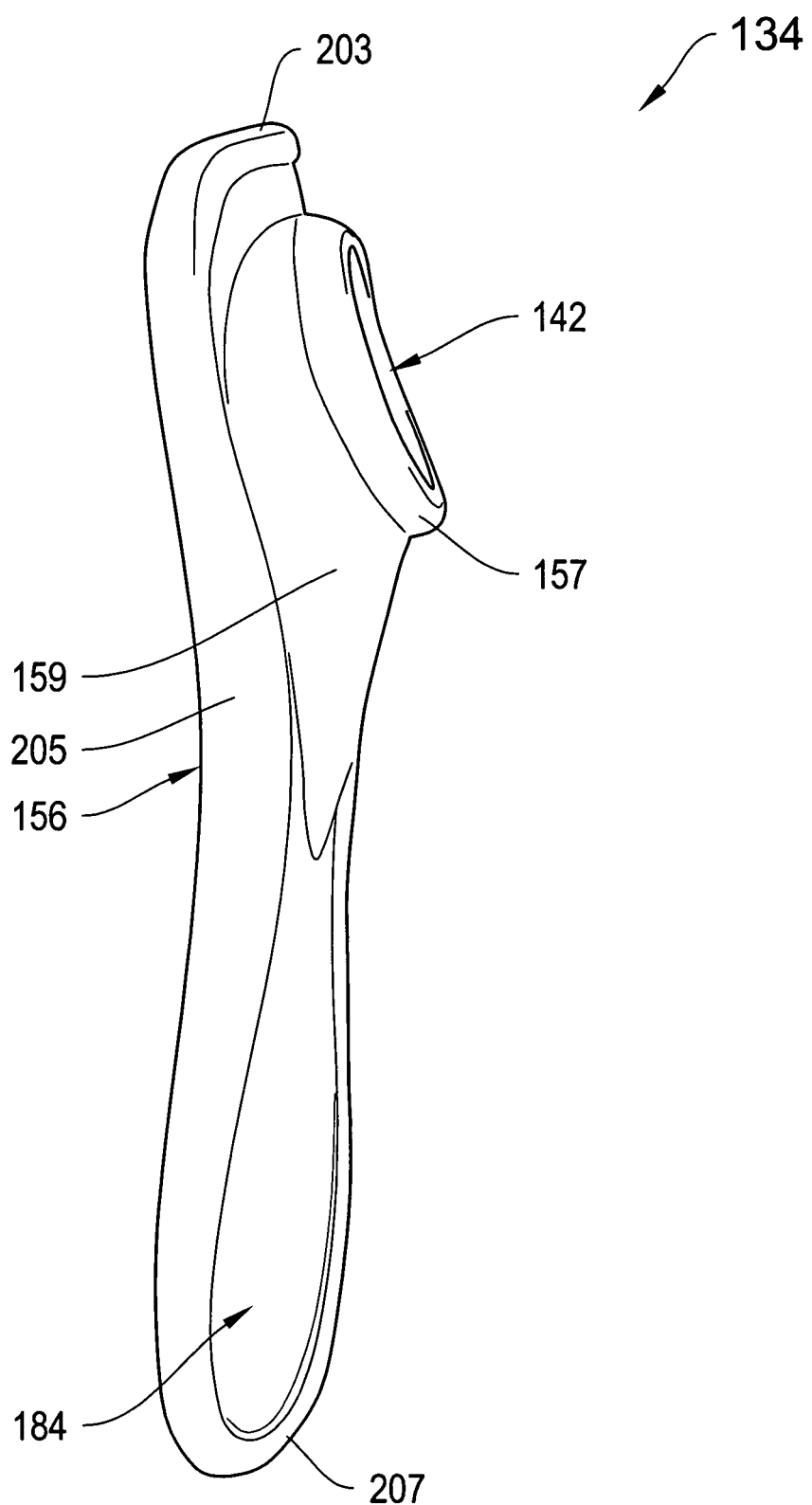
Figure 13C:
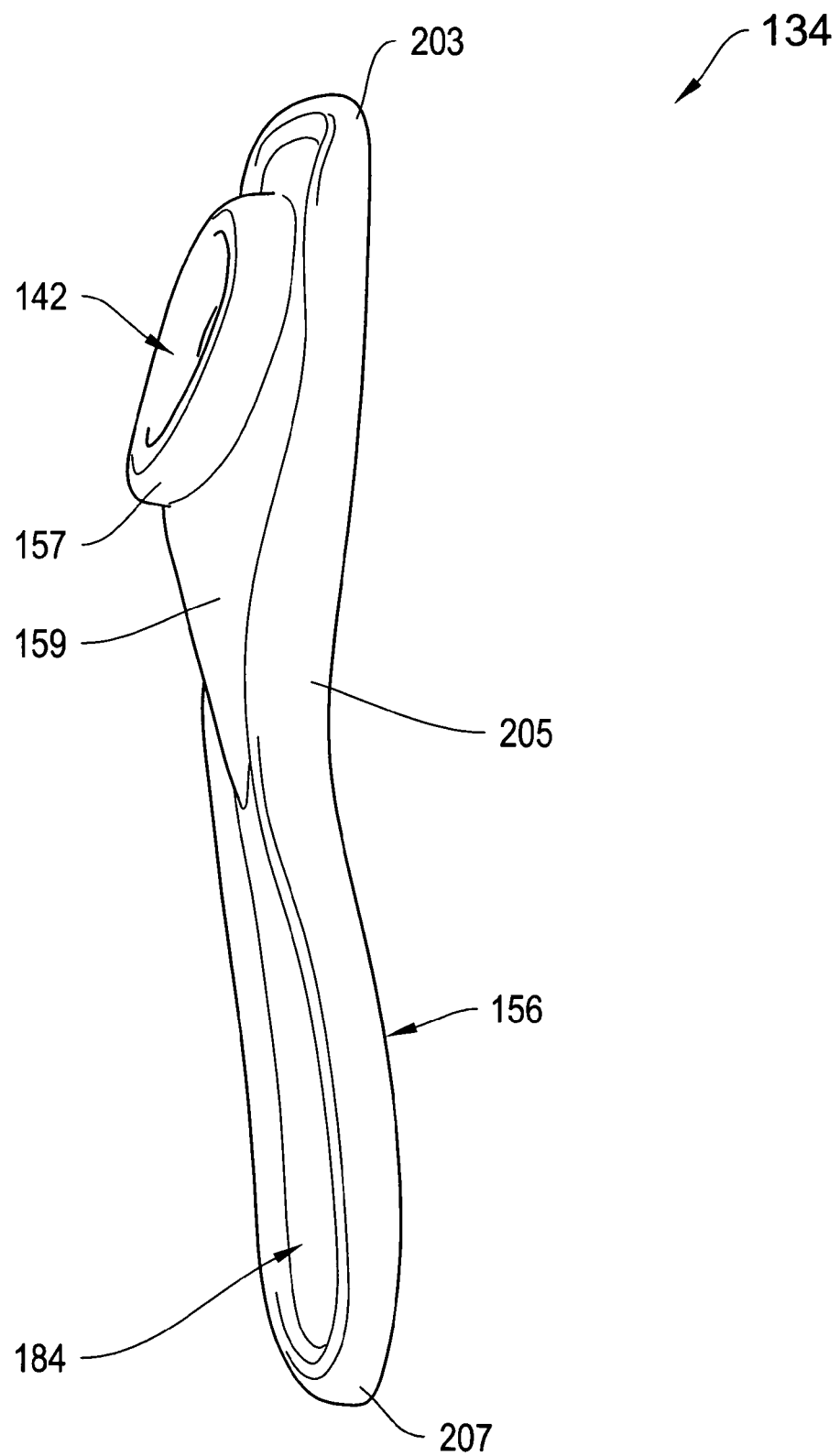
Figure 13D:
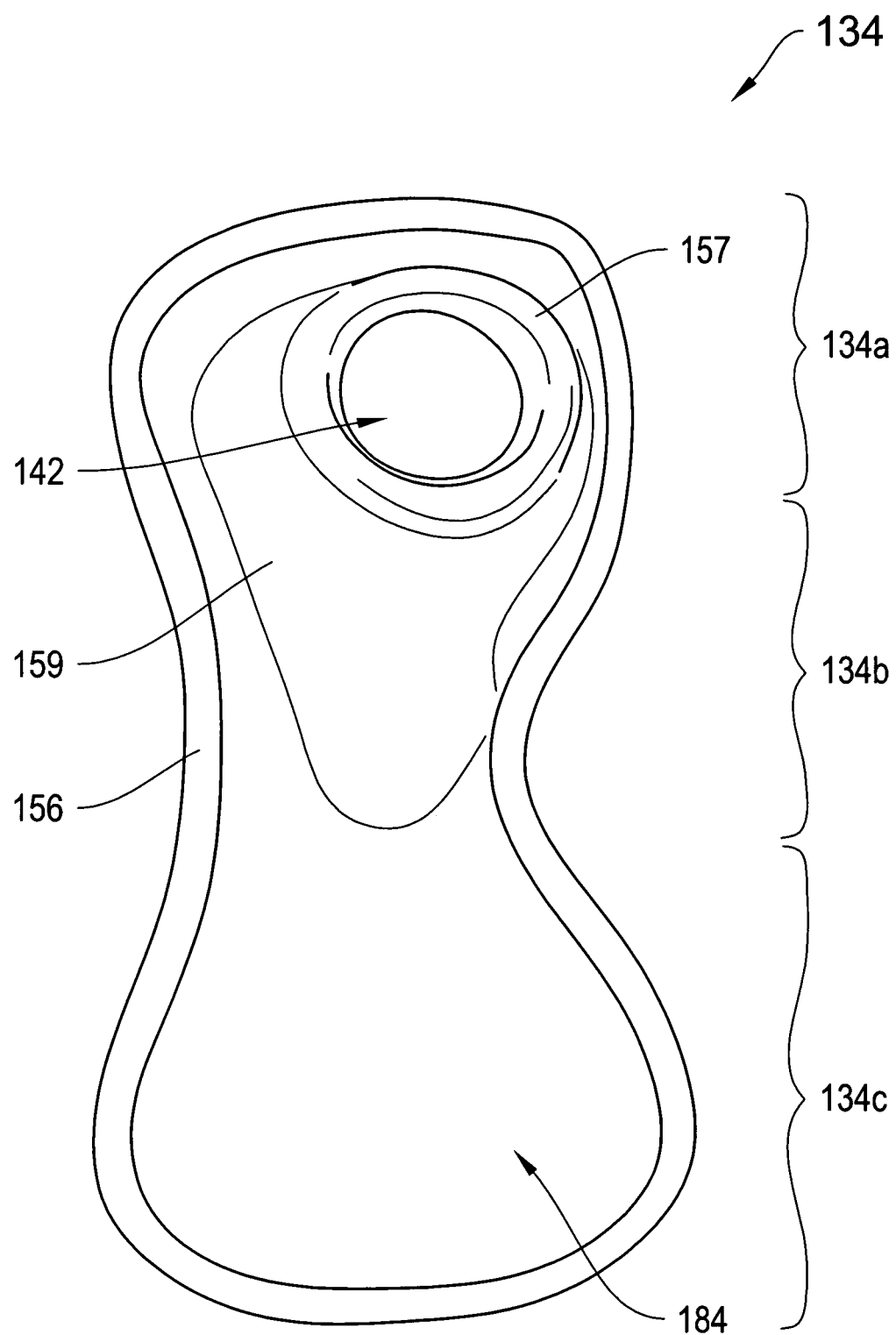

The medial outer shell 136 of the medial housing assembly 132 is more particularly shown in FIGS. 12A-12C, which depict exterior volar, interior volar, and exterior radial views of the outer medial shell 136. The medial outer shell 136 has an external face 135 and an internal face 137 that is adapted to receive and interfit with the inner support pad 134. The medial outer shell 136, as shown in FIGS. 11A-11B and 12A-12C, includes first 144 and second 145 ridges, which extend along the length of the medial shell 136 from about the proximal end 136*a* to about the distal end of the medial shell 136. The first ridge 144 is located on the ulnar side of the medial shell 136 and is bordered on its ends by two slots 146 and 147 through which the proximal 139 and distal 143 straps are threaded, as shown in FIGS. 11A-11B. The distal strap 143 is threaded into the distal slot 147 and secured in place with a fastener 151. The second ridge 145 extends along the radius side of the medial shell 136, and similarly is bordered by two slots 129 and 149, through which the opposite ends of the proximal 139 and distal 143 straps are threaded. While the distal end 136a of the medial shell 136 surrounds the aperture 142 for a patient's thumb, the proximal end 136c of the medial shell 136 includes several large apertures 160, 161, and 162 which expose the inner support pad 134 (the aperture 160 is not shown in FIGS. 12A-12B). According to one feature, the proximal section 132C of the inner support pad 134 contains a plurality of through-apertures 163, which, in combination with the apertures 160, 161, and 162 of the medial shell, permit ambient air to flow to the patient's forearm.

As shown in FIG. 11D and FIGS. 13A-13C, the inner support pad 134 has an internal face 182 configured to fit against the user's forearm, wrist and thumb, and an external face 184 adapted to receive and interfit with the outer medial shell 136. The inner support pad 134 is contoured to fit to a patient's hand, wrist, and forearm, as described above. In the depicted embodiment, the pad 134 is pre-formed by molding or other processes to be configured to the patient's hand and arm. In one exemplary process, according to one feature, in operation, a mold is taken of a patient's hand, wrist, and forearm, and the inner support pad 134 is formed from the mold to be contoured to fit the patient according to the mold.

The inner support pad 134 is configured to provide contoured support for the user's limb through one or more of various features, as more particularly depicted in FIGS. 13A-13D. FIGS. 13A-13D depict interior volar, exterior ulnar-side, and exterior radial-side views of the inner support pad 134. On exemplary feature of the pad 134 that allows it to provide for contoured support is its variable width. As shown, the pad 134 has a distal section 134a, sized sufficiently wide to enclose the volar side of a patient's hand, a tapered middle section 134b, which narrows to conform to the patient's wrist, and a proximal section 134c, which widens outward for placement along the patient's forearm, all surrounded by an outer rim 172. As another feature, as shown, in FIGS. 13B and 13C, the pad 134 is configured to have variable thickness for further providing contoured support. As shown, the outer rim 156 has a top rim 203 in the distal section 134a that thickens to a middle rim 205 in the mid-section 134b and tapers to a bottom rim 207 on the proximal section 134c.

As another feature, the pad 134 also provides contoured support by a contoured well 174 formed in the distal section 134a of the interior face 182 and shaped to fit around the patient's thumb. The well 174 slopes from the outer rim 172 to the aperture 142 on the interior face 182 and forms a prominence 159 on the exterior face 184 which slopes downward from the padded edge 157 of the aperture 142 to an outer rim 156 of the exterior face 184. The contoured support of the pad 134 is further enhanced by The tapered middle section 134b includes a depressed mid-ridge 176, as shown in FIG. 11D, which extends along the longitudinal midline of the support pad 134 from the distal section 134a to the proximal section 134c.

Another feature that allows the pad 134 to provide contoured support is a padded edge 157 that surrounds the through-aperture 142, as shown in FIGS. 11A-11B. As shown, the padded edge 157 is constructed as part of the inner support pad 134, which protrudes outwardly through the outer medial shell 136. The inner support pad 134 extends around the perimeter of the through-aperture 142 and rises to a height above the knuckle on the patient's thumb, as shown in FIG. 11B. The pad 134 also includes a plurality of small holes 163 as shown in FIG. 11D to allow ambient air to flow through the pad 134 to the limb.

The contoured support provided by the medial housing assembly 132 is further enhanced by the lateral housing assembly 138. The lateral housing assembly 138 is more particularly shown in FIGS. 11A, 11C, and 11D, and is similar to the lateral component 104 of casing 111 described above. As shown, the lateral housing assembly 138 includes an outer lateral shell 150 and an inner inflatable cell 148, similar to the cell 500 described above. According to one feature, the lateral housing assembly 138 fits over the dorsal side of a patient's right forearm. The lateral housing assembly 138 includes a valve 164, which can be used to inflate an air cell in the inner inflatable cell 148. The middle section 138b of the lateral housing assembly 138 includes an attachment member 180, through which the middle strap 141 can be threaded.

Figure 14A:
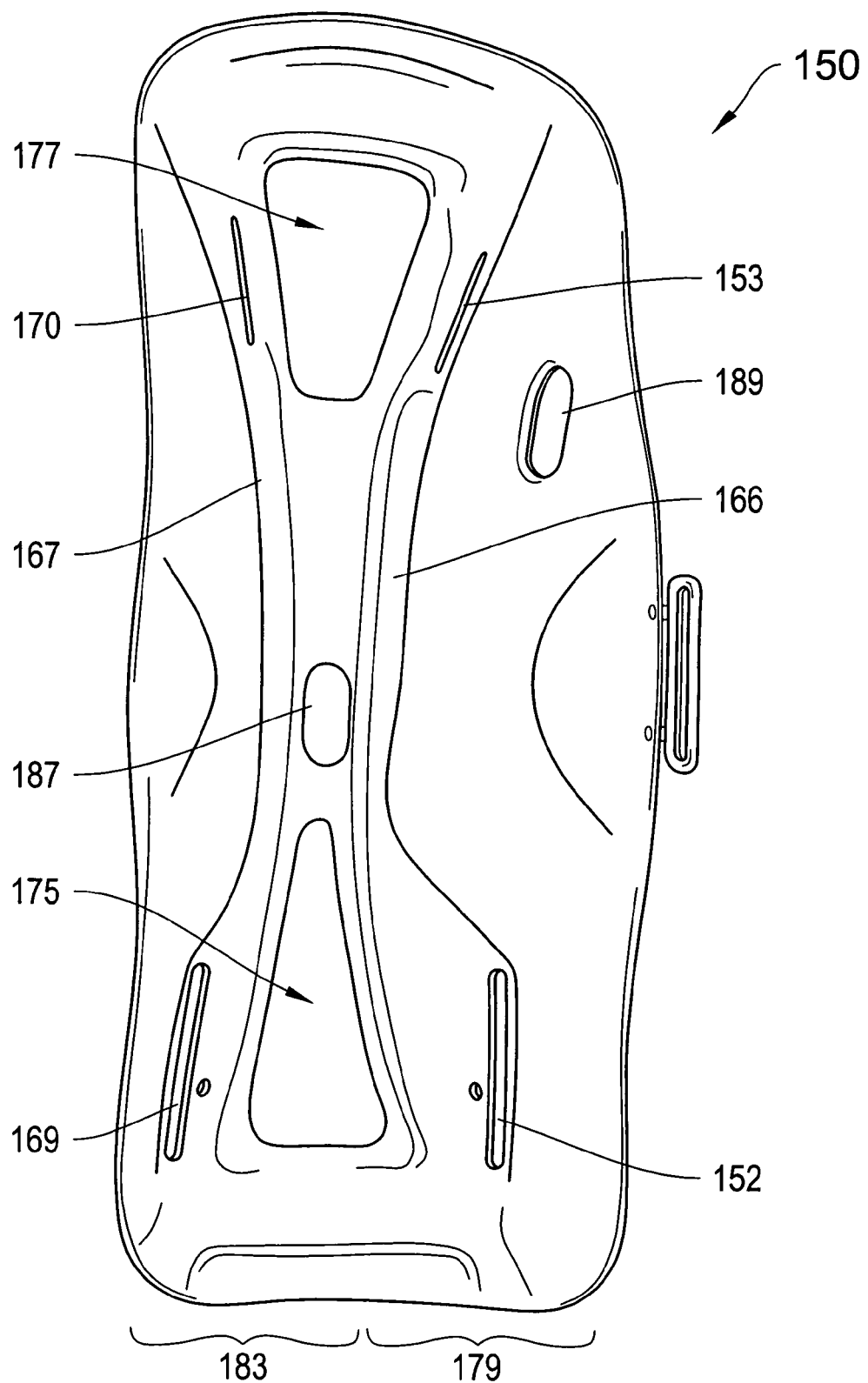
FIGS. 14A-14B depict an exemplary lateral outer shell used with the brace depicted in FIGS. 11A-11D.
Figure 14B:
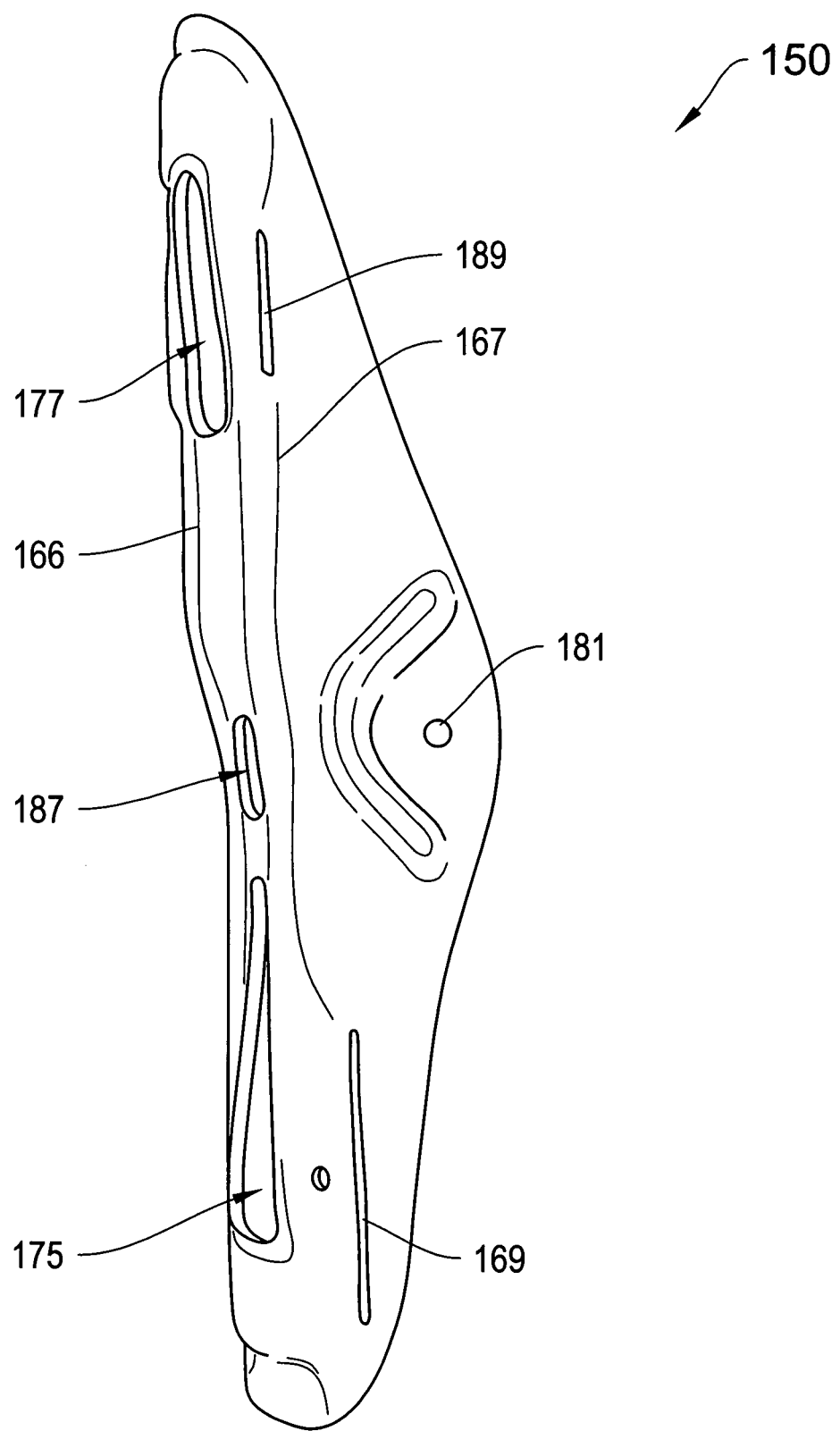
Figure 15:
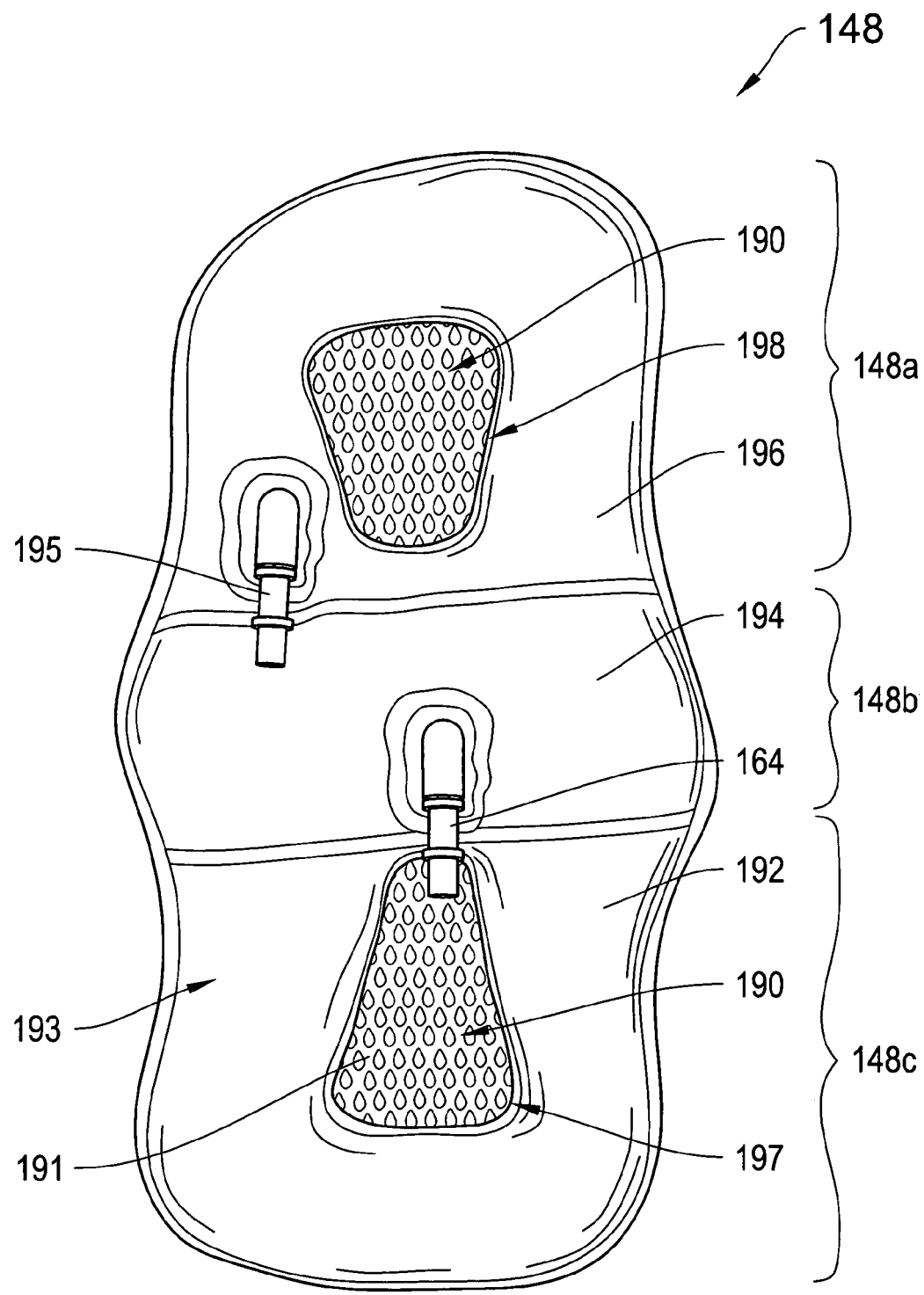
FIG. 15 depicts an exemplary inflatable cell used as a lateral inner support member with the brace depicted in FIGS. 11A-11D.

The lateral housing assembly 138 is depicted more particularly in FIGS. 14A-14B and FIG. 15. FIGS. 14A-14B show interior dorsal and exterior ulnar views of the outer lateral shell 150, respectively. The lateral shell 150 includes first 166 and second 167 ridges, which extend along the length of the lateral shell 150. The first ridge 166 is located on the radial side 179 of the lateral shell 150, and includes proximal 152 and distal 153 slots, through which the proximal 139 and distal 143 straps are threaded, as shown in FIG. 11C. The proximal strap 139 is threaded into the proximal slot 152 and secured in place with a fastener 168. The second ridge 167 is located on the ulnar side of the lateral shell 150, and includes proximal 169 and distal 170 slots, through which the proximal 139 and distal 143 straps are threaded. Similar to the configuration on the radius side, the proximal strap 139 is threaded into the proximal slot 169 and secured in place with a fastener 173. The lateral shell 150 additionally includes the attachment member 180 on the radius side, through which the middle strap 141 is threaded, and a fastener aperture 181 on the ulnar side, which is used with a fastener to secure the middle strap 141 to the ulnar side of the lateral shell 150.

As shown in FIG. 14A, the lateral shell 150 also includes proximal 175 and distal 177 apertures positioned along the midline, which expose the outer surface 190 of the inner inflatable cell 148. According to one feature, the apertures 175 and 177 permit airflow to the patient's forearm and hand. Additionally, the lateral shell 150 includes smaller middle 187 and distal radius 189 apertures, through which the valves 164 and 195 of the inner inflatable cell 148 (shown in FIG. 14C) emerge.

FIG. 15 more particularly depicts the inner inflatable cell 148 shown in FIGS. 11A-11D, which is contains inflation fluid for providing pressurized support to the limb, similar to the cell 500 described above and is used with the lateral housing assembly 138. The inflatable cell 148 includes a distal section 148a, a middle section 148b, and a proximal section 148c. Inner inflatable cell 148 includes an interior face 185, shown in FIG. 11D, and an exterior face 193 shown in FIG. 15 and includes a mesh cover 191 across its interior face 185, the mesh cover 191 being visible through the apertures 197 and 198. The interior face 185 of the inflatable cell 148 is flexible and therefore adapted to fit to a patient's hand, wrist, and forearm in a contoured manner. In an optional embodiment, the inner face 185 of the cell 148 has an additional layer of padding to form a depressed ridge 178, which extends from the distal section 148a through the middle section 148b toward to the proximal section 148c of the inflatable cell 148, as shown in FIG. 11D. This ridge 178 assists in fitting the cell 148 to the user's limb.

In the depicted embodiment, the cell 148 is formed of a plurality of inflatable compartments including proximal 192, middle 194, and distal 196 inflatable compartments and has first 164 and second 195 valves to provide inflation fluid to the compartments. The first valve 164 is used to inflate the middle compartment 194, while the second valve 195 is used to inflate the proximal 192 and distal 196 compartments. The proximal 192 and distal 196 compartments form a continuous inflatable cell that extends under the middle compartment 194. The inflation pressure of the inflation fluid in the compartments can be selectively adjusted by the user as desired.

In another aspect, the cell 148 is configured to provide balanced inflation around the perimeter of the brace 130, similar to the perimeter loading described above with reference to the cell 500 in FIG. 4. To this end, the proximal 192 and distal 196 compartments include proximal 197 and a distal 198 apertures, respectively that extend across the thickness of the cell 148, thereby impeding the cell 148 from inflating over the regions of the apertures 197 and 198. The inflation fluid distributes in the compartments 192 and 196 around the apertures 192 and 196 and along the perimeter or mid-sections of the compartments 192 and 196. This perimeter fluid distribution impedes the cell 148 from over-inflating across its mid-section (like a football) and more evenly distributes the inflation pressure about the limb. The inflation pressure level and distribution within the cell 148 can also be adjusted by increasing or decreasing the pressure within the middle compartment 194.

With continued reference to FIGS. 11A-11D, the brace 130 includes straps to secure the brace 130 to the user's forearm. As shown, the medial housing assembly 132 is attached to the lateral housing assembly 138 by the straps 139, 141, and 143 to secure the brace 130 around a patient's forearm. According to one embodiment, the straps 139, 141, and 143 loop through slots, such as slots 146, 147, 148, 149, 152, 153, 169, 170 and 180, in the medial 132 and lateral 138 housing assemblies, and fold back over such that each strap 139, 141, and 143 attaches to itself using a Velcro material. This permits adjustability of the straps 139, 141, and 143. However, any suitable strap material and any suitable attachment mechanism may be used.

Figure 16A:
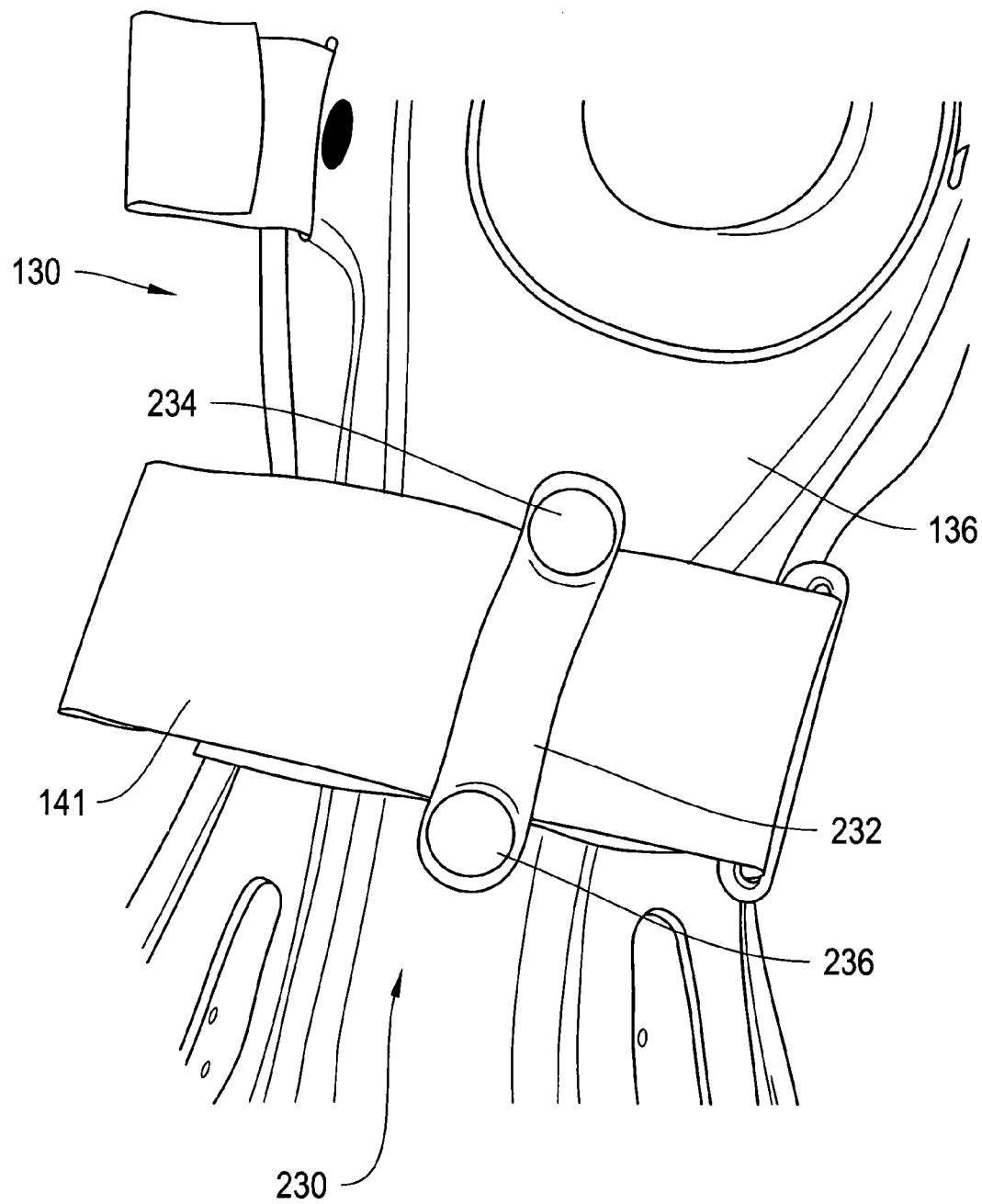
FIGS. 16A-16B depict exemplary embodiments of a patient compliance monitoring assembly that may be applied with a brace.

According to another alternative modification, the brace 130 includes a compliance monitoring assembly to be applied by a physician to help the physician identify whether a patient has prematurely removed the brace 130. FIG. 16A depicts a close-up view of the brace 130 having an exemplary embodiment of a compliance monitoring assembly 230 applied thereto. The compliance monitoring assembly 230 includes a compliance strap 232, and first 234 and second 236 non-reusable fasteners attached to the middle strap 141 of the brace 130. The first 234 and second 236 fasteners are affixed to the middle strap 141 and to the outer medial shell 136 by the at about the lateral edges of the strap 232. The compliance monitoring assembly 230 cannot be disengaged from the brace 130 without removing the non-reusable fasteners. Moreover, when the compliance monitoring assembly 230 is affixed to the brace 130 as shown, the strap 141 cannot be adjusted or the brace 130 removed from the patient's limb without disengaging the fasteners 234 and 236, and once the fasteners 234 and 236 are removed, the compliance monitoring assembly 230 cannot be reattached using the same fasteners 234 and 236. Thus, a physician can identify whether a patient has disengaged the original fasteners 234 and 236 and inquire whether the patient has also removed the brace 130. The fasteners 234 and 236 are rivets, snaps, pins, nails, staples, or any other suitable attachment mechanisms. Additionally, the fasteners 234 and 236 may be positioned in any suitable location on the compliance strap 232 and may affix the compliance strap 244 to any suitable location on the brace 130.

Figure 16B:
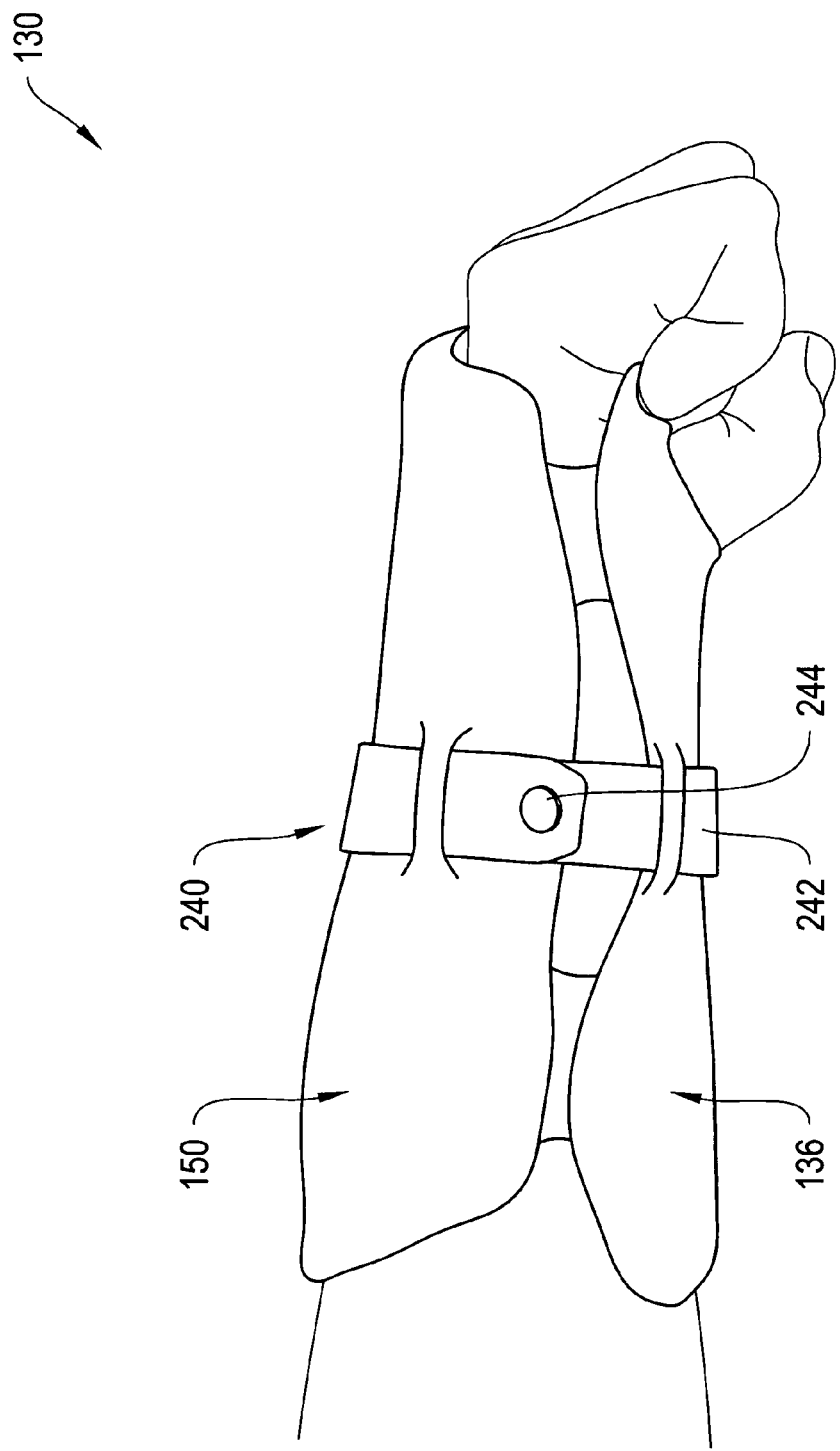

FIG. 16B depicts an alternative compliance monitoring assembly 240 that includes a compliance strap 242 and a non-reusable fastener 244 for use with the brace 130. The compliance strap 242 is an attachment strap, similar to the middle strap 141 shown in FIGS. 11A-11C, which extends about the brace 130 around the perimeter of the patient's forearm and secures the brace 130 about the patient's forearm by the fastener 244. The non-reusable fastener 244 is positioned at about the center of the width of the strap 242. In an optional embodiment, the fastener 244 may also be configured to affix the compliance strap 244 directly to the outer lateral shell 150 of the brace 130. According to alternative illustrative embodiments, the fastener 244 may be positioned in any suitable location on the compliance strap 242 and may affix the compliance strap 242 to any suitable location on the brace 130. As described above with respect to the fasteners 234 and 236, fastener 244 is not reusable, such that a physician can identify whether a patient has disengaged the fastener 244 as evidence to suggest whether the patient has removed the brace 130.

Figure 17A:
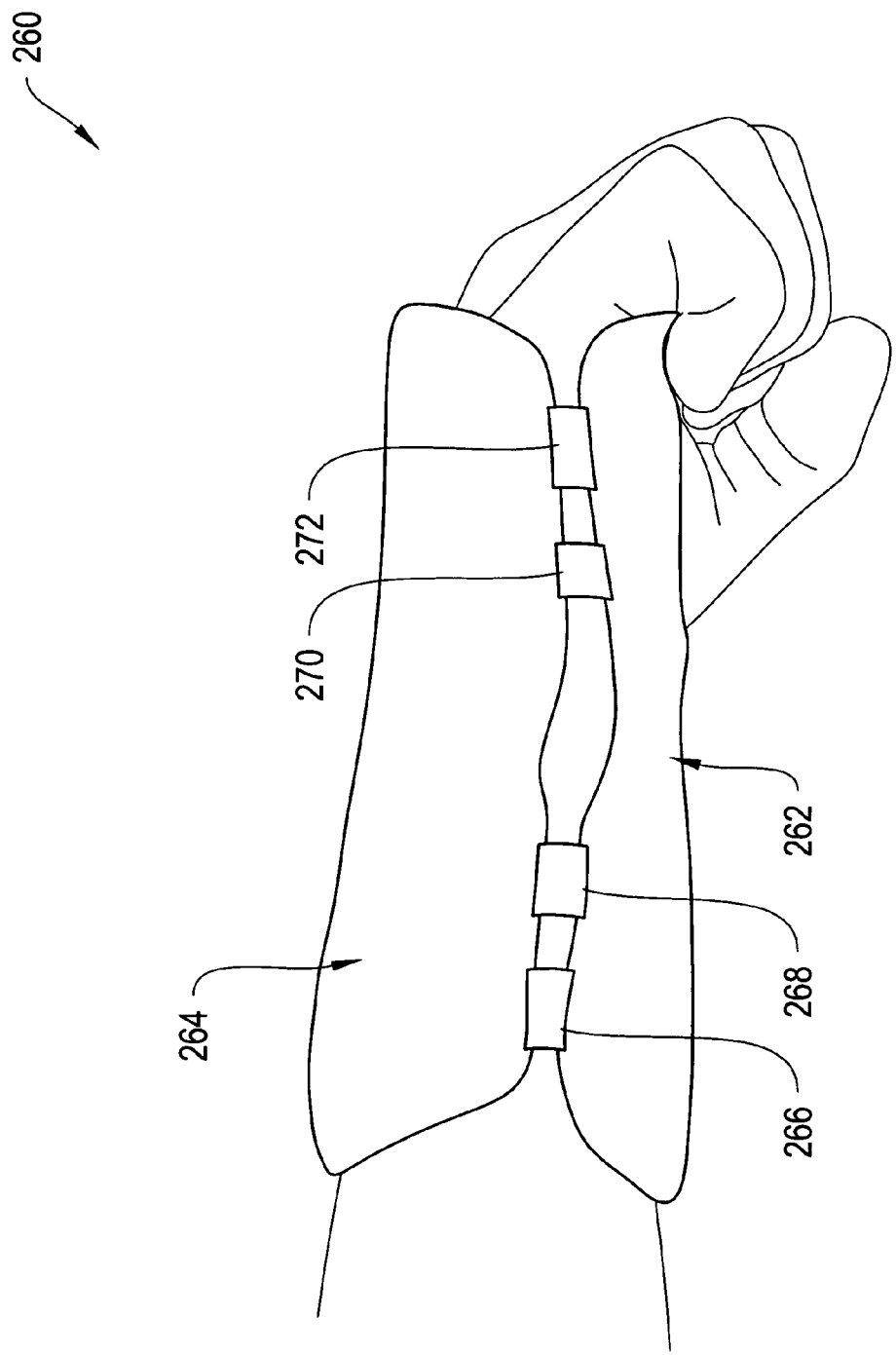
FIGS. 17A-17B depict exemplary embodiments of a unitary outer shell system that may be used with a brace.

In another exemplary alternative modification, the braces 130 and 100 are configured with a unitary shell system in place of the separate lateral and medial outer shells described above, the unitary shell system having a connector assembly adapted to pivotally adjoin the lateral and medial shells on one side of the brace. FIG. 17A depicts an example of such a brace 260 that includes a medial shell 262 connected to a lateral shell 264 by a connector assembly that includes first 266, second 268, third 270 and fourth 272 hinges. The hinges 266, 268, 270 and 272 connect the medial shell 262 to the lateral shell 264 along the ulnar side of the brace 260, allowing the shell 262 to pivot about the shell 264 at the hinges on that side. The hinges may be standard mechanical hinges, soft hinges, adjustable hinges, or any other suitable hinges. Additionally, while not shown, adjustable straps, such as 139, 141, or any other suitable mechanical fastener, are applied to secure the brace 280 to the limb. Moreover, one or more compressible members may be included within the shells, as described above.

Figure 17B:
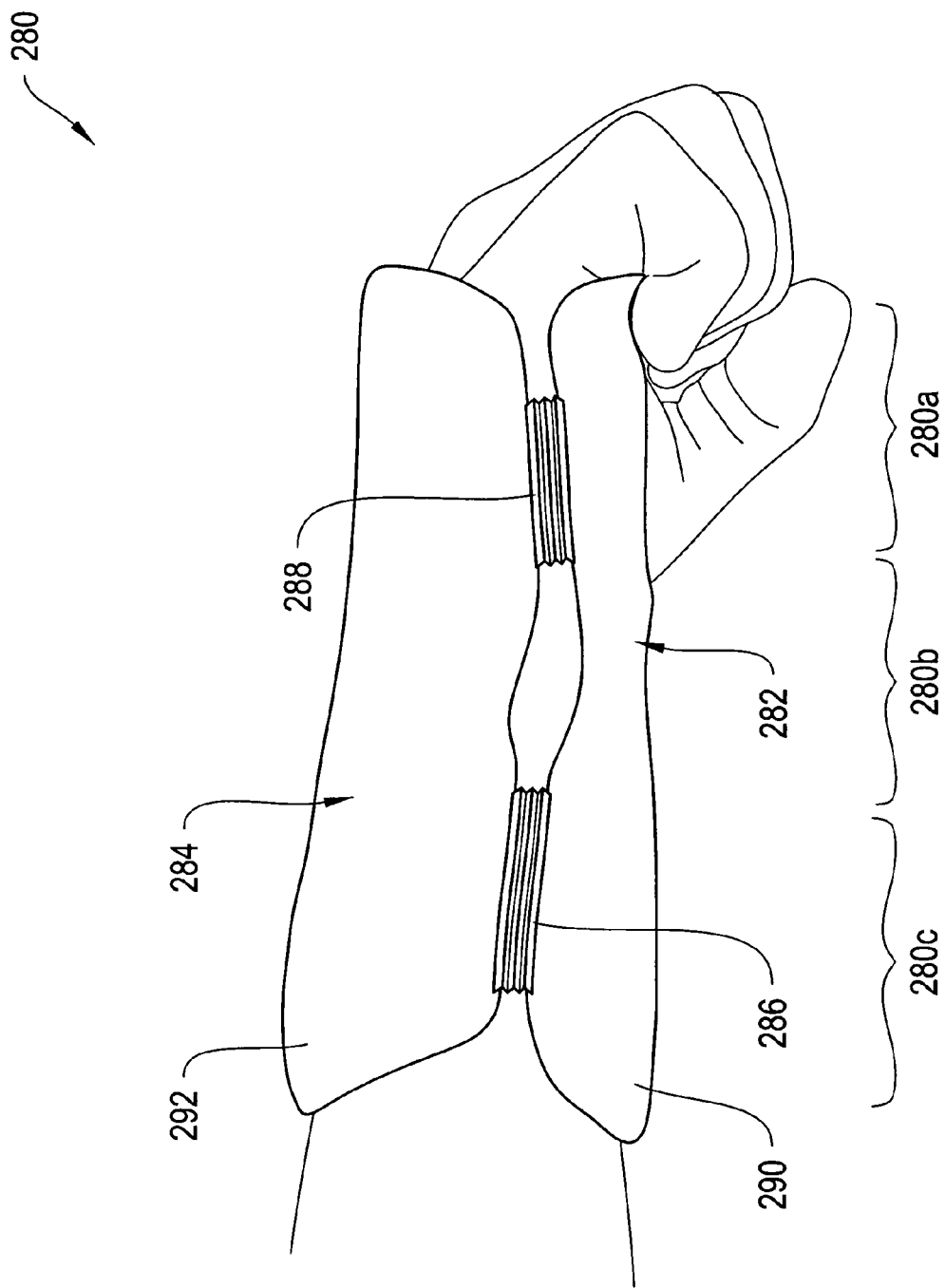

FIG. 17B depicts an alternative configuration of a connector assembly for use with a brace 280 having a unitary shell system. The depicted brace 280 includes a medial housing assembly 282, having a distal end 280a configured and contoured to fit in a patient's palm, a lateral housing assembly 284, and first 286 and second 288 connection membranes that adjoin exterior shell portions 290 and 292 of the medial 282 and lateral 284 assemblies along the ulnar side of the brace 280. The connection membranes 286 and 288 are accordion-like, having separate faces adapted to collapse and expand as the membranes 286 and 288 contract and expand. The medial housing assembly 282 and the lateral housing assembly 284 are similar to the medial housing assembly 132 and the lateral housing assembly 138, respectively, of the brace 130 described above, except that the housing assemblies 282 and 284 are permanently attached at their exterior shells 290 and 292 by connection membranes 286 and 288, resulting in a unitary exterior shell for the brace 280 that allows the housing assemblies 282 and 284 to pivot about each other along the ulnar side of the brace 280. The connection membranes 286 and 288 may be any suitable connection elements, such as a membrane molded to the shells 290 and 292, and may be configured from polymer, canvas, or other suitable fabric. In an alternative implementation, the outer shells 290 and 292 are continuously molded from a single piece of material, and one or more connecting membranes are formed as a crease between the shells 290 and 292. Though not shown, it will be appreciated that a suitable connection membrane may be formed on the radial side of the brace.

In another exemplary modification, the braces 100 and 130 are adapted to treat injured legs ankles. FIG. 18 depicts an exemplary embodiment of such a brace 960, including a casing 961 having top 961*a* and bottom 961*b* portions. Also shown is a medial liner 969 and compressible material 970 at least partially enclosed by the casing 961.

The brace 960 may be secured to a user's leg 958 by top straps 964 and bottom straps 965. FIG. 18 also depicts a support 967 for connecting one portion of a user's leg 958*a* to another portion 9582*b*, extending across the ankle. The brace 960 includes, in certain embodiments, top and bottom compressible members 969*a* and 969*b* (not shown) of the compressible material described above. The brace 960 is thus adapted to impede inversion, eversion, plantar flexion, and dorsal flexion of an ankle.

In another aspect, the invention includes methods for the use and manufacture of braces. The various features and components described herein may be readily adaptable to methods of manufacture. For example, a brace may be manufactured as an adjustable casing by providing a lateral portion comprising a casing and compressible material, providing a medial portion comprising a casing and compressible material, and providing a strap. A liner may also be provided with the lateral portion, medial portion, or both. Those skilled in the art will recognize a number of other methods of manufacture and use. For example, similar methods may be applied to manufacture braces having volar and dorsal portions. The methods for manufacturing may provide an adjustable casing that is adapted to fit across the injured limb e.g. the wrist and in contact with another of a user's limbs sufficient to impede flexion of the user's limb. In certain embodiments the brace is adapted to impede at least one of palmar flexion, dorsi flexion, radial deviation, ulnar deviation, pronation of the forearm, supination of the forearm. The method may be further exploited by providing compressible material, and enclosing at least part of the compressible material in the casing. In certain embodiments a brace has at least one component adapted to impede one or more of inversion, eversion, plantar flexion, and dorsal flexion of an ankle.

In another embodiment, a brace may be used to treat an injured limb. For example, an injured wrist may be treated by providing compressible material that is at least partially enclosed in an adjustable casing. The brace may have at least one component e.g., part of the adjustable casing, a rod or other stiff item applied to the brace, etc. adapted to fit across the wrist and in contact with a user's hand sufficient to impede at least one of palmar flexion, dorsi flexion, radial deviation, ulnar deviation, pronation of the forearm, supination of the forearm. In certain embodiments the wrist is treated by impeding palmar flexion, dorsi flexion, radial deviation, and/or ulnar deviation, without impeding pronation or supination of the forearm. Such methods typically involve fitting the casing to the user's wrist. Similarly, an injured ankle may be treated by applying compressible material enclosed at least partially in an adjustable casing to an ankle, the casing having at least one component adapted to impede one or more of flexion, inversion or eversion of the ankle.

The figures describe exemplary embodiments of the invention but are not limiting. The embodiments shown for a right hand can be configured to apply to a left hand. The braces and methods described herein can be adapted and modified for other applications, including for use with ankles, elbows, knees, or shoulders. Such additions and modifications will not depart from the scope hereof. Accordingly, the description and examples set forth herein are for illustration purposes only, and are not to be understood as limiting in any way. All references cited herein are hereby incorporated by reference in their entirety.

The invention claimed is:

1. A brace for supporting an injured wrist, comprising:
an adjustable casing adapted to impede flexion of the injured wrist and having a lateral shell and a medial shell and a mechanical fastener adapted to tighten and loosen the casing, and
a first compressible member at least partially enclosed by the medial shell of the adjustable casing and having inner and outer surfaces, wherein the inner surface is pre-formed to contoure the medial side of a user's wrist, the inner surface including a pre-formed interior well having an edge that is coextensive with a distal region of the inner surface, the interior well defining a pre-formed depression in the distal region that extends from the edge in a direction toward the tip of the user's thumb to allow the interior well to surround a portion of the user's thumb, and wherein the pre-formed depression formed by the interior well also defines a corresponding prominence on the outer surface of the first compressible member.

2. The brace of claim 1, comprising a second compressible member at least partially enclosed by the lateral shell of the adjustable casing and including at least one inflatable cell having a distal compartment, a middle compartment, and a proximal compartment, wherein a portion of the distal compartment and a portion of the proximal compartment extend under the middle compartment.

3. The brace of claim 2, wherein the proximal and distal compartments form a continuous inflatable cell that extends under the middle compartment.

4. The brace of claim 2, wherein the middle compartment and the proximal compartment are independently inflatable.

5. The brace of claim 1, wherein the interior well includes a through-aperture for receiving the user's thumb.

6. The brace of claim 5, wherein the through-aperture includes a thumb support ring disposed substantially about the through-aperture and extending above a knuckle on the user's thumb.

7. The brace of claim 1, wherein the first compressible member includes a distal region, a mid-region, and a proximal region and wherein the mid-region has a width that is smaller than a width of the distal region and a width of the proximal region.

8. The brace of claim 1, wherein the first compressible member includes a distal region, a mid-region, and a proximal region and wherein the mid-region has a thickness that is smaller than a thickness of the distal region and a thickness of the proximal region.

9. The brace of claim 1, wherein the mechanical fastener includes at least one strap connecting the medial and lateral shells.

10. The brace of claim 1, wherein the first compressible member is a foam pad.

11. The device of claim 1, wherein the medial shell includes an inner surface that is pre-formed and contoured to interface with the outer surface of the first compressible member.

12. The device of claim 1, wherein the medial shell includes an aperture, and a portion of the prominence of the first compressible member protrudes through the aperture.

13. The brace of claim 1, wherein the outer surface of the first compressible member is pre-formed and contoured to interface with the medial shell.

14. The device of claim 1, wherein the interior well has a dome-like shape.

15. The device of claim 1, wherein the lateral shell includes an opening for connecting a valve to a fluid source.

16. The device of claim 5, wherein the through-aperture extends into the user's palm.

17. The brace of claim 2, comprising a first valve and a second valve, wherein the first valve is adapted to inflate the middle compartment and the second valve is adapted to inflate the proximal and the distal compartments.

18. The brace of claim 2, wherein the inflatable cell includes at least one pocket in each of the distal and the proximal compartments to impede the inflatable cell from expanding unevenly across the inflatable cell.

19. The brace of claim 18, wherein the middle compartment spans between the pockets located in the distal and proximal compartments.

20. The device of claim 12, wherein the prominence of the first compressible member forms a circular pad around the thumb.

21. The device of claim 12, wherein the prominence of the first compressible member extends further along the thumb than the aperture.

22. The device of claim 12, wherein the prominence and aperture encircle the thumb.

23. The device of claim 22, wherein the prominence is spaced between the thumb and the aperture.

\* \* \* \* \*